United States Patent
Holmes et al.

(10) Patent No.: US 7,828,735 B2
(45) Date of Patent: Nov. 9, 2010

(54) METHODS FOR PROVIDING DIAGNOSTIC INFORMATION USING ENDOCARDIAL SURFACE DATA FOR A PATIENT'S HEART

(75) Inventors: Jeffrey W. Holmes, New York, NY (US); Kevin D. Costa, New York, NY (US); Susan L. Herz, New York, NY (US); Christopher M. Ingrassia, New York, NY (US)

(73) Assignee: The Trustees of Columbia in the City of New York, New York, NY (US)

( * ) Notice: Subject to any disclaimer, the term of this patent is extended or adjusted under 35 U.S.C. 154(b) by 852 days.

(21) Appl. No.: 11/801,457

(22) Filed: May 10, 2007

(65) Prior Publication Data

US 2008/0077032 A1    Mar. 27, 2008

Related U.S. Application Data

(60) Provisional application No. 60/799,460, filed on May 11, 2006, provisional application No. 60/802,942, filed on May 23, 2006.

(51) Int. Cl.
*A61B 8/06* (2006.01)
(52) U.S. Cl. .................. 600/450; 600/523; 600/508
(58) Field of Classification Search .......... 600/410, 600/424, 425, 450, 508, 587
See application file for complete search history.

(56) References Cited

OTHER PUBLICATIONS

Herz, S.L. et al., "Reducing Motion Artifact in Three-Dimensional Left Ventricular Wall Motion Analysis," abstract. 2005 Summer Bioengineering Conference, Jun. 22-26, Vail Cascade Resort & Spa, Vail, Colorado.

Costa, K.D. et al., "Finite element analysis of 3-D left venticular endocardial wall motion," abstract., World Congress on Medical Physics and Biomedical Engineering, Sydney, Australia, 2003.

Fomovsky, G.M. et al., "Relating in vivo and ex vivo mechanics in healing myocardial scar tissue," abstract, 2005 Summer Bioengineering Conference, Jun. 22-26, Vail Cascade Resort & Spa, Vail, Colorado.

Hughes, T.J.R. "The Finite Element Method" Chapters 1.1-1.16 and 3.6-3.11, Prentice-Hall, Inc., Englewood Cliffs, N.J., 1987.

Noble, B. et al., "The Method of Least Squares," Applied Linear Algebra—Section 2.6, pp. 57-63, Prentice-Hall, Inc., Englewood Cliffs, N.J., 1977.

Angelini ED, Homma S, Pearson G, Holmes JW, Laine AF. Segmentation of real-time three dimensional ultrasound for quantification of ventricular function: a clinical study on right and left ventricles. Ultrasound Med Biol, 31:1143-1158, 2005.

Angelini ED, Laine AF, Takuma S, Holmes JW, Homma S. LV volume quantification via spatio-temporal analysis of real-time 3D echocardiography. IEEE Trans Med Imag, 20:457-469, 2001.

(Continued)

*Primary Examiner*—Carl H. Layno
*Assistant Examiner*—Jon-Eric C. Morales
(74) *Attorney, Agent, or Firm*—Wilmer Cutler Pickering Hale and Dorr LLP

(57) ABSTRACT

Methods for providing diagnostic information using endocardial surface data for a patient's heart are described herein. In some embodiments, endocardial surface data for the left ventricle of a heart is received. The endocardial surface data represents the endocardial surface of the left ventricle at multiple times over a heartbeat and is obtained using a volumetric imaging application. A representation in prolate spheroidal coordinates of the endocardial surface of the left ventricle at least a portion of the multiple times is generated using the endocardial surface data. The prolate spheroidal coordinates include a longitudinal angular coordinate $\mu$, a circumferential angular coordinate $\theta$, and a coordinate $\lambda$ as a function of longitudinal angular coordinate $\mu$ and circumferential angular coordinate $\theta$. A measure that provides diagnostic information related to the left ventricle is computed based at least on part on the value of coordinate $\lambda$.

26 Claims, 19 Drawing Sheets

OTHER PUBLICATIONS

Armstrong WF, O'Donnell J, Ryan T, Feigenbaum H. Effect of prior myocardial infarction and extent and location of coronary disease on accuracy of exercise echocardiography. J Am Coll Cardiol, 10:531-538, 1987.

Armstrong WF, Pellikka PA, Ryan T, Crouse L, Zoghbi WA. Stress echocardiography: recommendations for performance and interpretation of stress echocardiography. Stress Echocardiography Task Force of the Nomenclature and Standards Committee of the American Society of Echocardiography. J Am Soc Echocardiogr, 11:97-104, 1998.

Award Abstract #0201617, http://nsf.gov/awardsearch/showAward.do?AwardNumber=0201617, Initial Amendment Date May 2, 2002, Latest Amendment Date Apr. 29, 2004.

Axel L, Goncalves RC, Bloomgarden D. Regional heart wall motion: two-dimensional analysis and functional imaging with MR imaging. Radiology, 183:745-50, 1992.

Axel L, Montillo A, Kim D. Tagged magnetic resonance imaging of the heart: a survey. Med Image Anal, 9:376-93, 2005.

Azhari H, Weiss JL, Rogers WJ, Siu CO, Zerhouni EA, Shapiro EP. Noninvasive quantification of principal strains in normal canine hearts using tagged MRI images in 3-D. Am J Physiol Heart Circ Physiol, 264:H205-H216, 1993.

Barron JL, Fleet D, al. e. Performance of optical flow techniques. Int J Comp Vision, 12:43-77, 1994.

Biagini E, Elhendy A, Bax JJ, Schinkel AF, Poldermans D. The use of stress echocardiography for prognostication in coronary artery disease: an overview. Curr Opin Cardiol, 20:386-94, 2005.

Buchalter MB, Weiss JL, Rogers WJ, Zerhouni EA, Weisfeldt ML, Beyar R, Shapiro EP. Noninvasive quantification of left ventricular rotational deformation in normal humans using magnetic resonance imaging myocardial tagging. Circulation, 81:1236-44, 1990.

Cheitlin MD, Armstrong WF, Aurigemma GP, Beller GA, Bierman FZ, Davis JL, Douglas PS, Faxon DP, Gillam LD, Kimball TR, Kussmaul WG, Pearlman AS, Philbrick JT, Rakowski H, Thys DM, Antman EM, Smith SC, Jr., Alpert JS, Gregoratos G, Anderson JL, Hiratzka LF, Hunt SA, Fuster V, Jacobs AK, Gibbons RJ, Russell RO. ACC/AHA/ASE 2003 guideline update for the clinical application of echocardiography: summary article: a report of the American College of Cardiology/American Heart Association Task Force on Practice Guidelines (ACC/AHA/ASE Committee to Update the 1997 Guidelines for the Clinical Application of Echocardiography). Circulation, 108:1146-62, 2003.

Chen X, Xie H, Erkamp R, Kim K, Jia C, Rubin JM, O'Donnell M. 3-D correlation-based speckle tracking. Ultrason Imaging, 27:21-36, 2005.

Chuang ML, Parker RA, Riley MF, Reilly MA, Johnson RB, Korley VJ, Lerner AB, Douglas PS. Three-dimensional echocardiography improves accuracy and compensates for sonographer inexperience in assessment of left ventricular ejection fraction. J Am Soc Echocardiogr, 12:290-9, 1999.

Corsi C, Lang RM, Veronesi F, Weinert L, Caiani EG, MacEneaney P, Lamberti C, Mor-Avi V. Volumetric quantification of global and regional left ventricular function from real-time three-dimensional echocardiographic images. Circulation, 112:1161-70, 2005.

Costa KD, Holmes JW, McCulloch AD. Modelling cardiac mechanical properties in three dimensions. Phil Trans R Soc Lond A, 359:1233-1250, 2001.

Costa KD, Hunter PJ, Wayne JS, Waldman LK, Guccione JM, McCulloch AD. A three-dimensional finite element method for large elastic deformations of ventricular myocardium: II—Prolate spheroidal coordinates. J Biomech Eng, 118:464-472, 1996.

D'Hooge J, Heimdal A, Jamal F, Kukulski T, Bijnens B, Rademakers F, Hatle L, Suetens P, Sutherland GR. Regional strain and strain rate measurements by cardiac ultrasound: principles, implementation and limitations. Eur J Echocardiogr, 1:154-70, 2000.

Danias PG, Papaioannou GI, Ahlberg AW, O'Sullivan DM, Mann A, Boden WE, Heller GV. Usefulness of electrocardiographic-gated stress technetium-99m sestamibi single-photon emission computed tomography to differentiate ischemic from nonischemic cardiomyopathy. Am J Cardiol, 94:14-9, 2004.

DeCara JM, Lang RM. Interpretation of left ventricular wall motion during stress testing. Echocardiography, 20:643-58, 2003.

Dolan MS, Riad K, El-Shafei A, Puri S, Tamirisa K, Bierig M, St Vrain J, McKinney L, Havens E, Habermehl K, Pyatt L, Kern M, Labovitz AJ. Effect of intravenous contrast for left ventricular opacification and border definition on sensitivity and specificity of dobutamine stress echocardiography compared with coronary angiography in technically difficult patients. Am Heart J, 142:908-15, 2001.

Duan Q, Angelini ED, Herz SL, Gerard O, Allain P, Ingrassia CM, Costa KD, Holmes JW, Homma S, Laine AF. Tracking of LV endocardial surface on real-time three-dimensional ultrasound with optical flow. Frangi AF, Radeva PI, Santos A, Hernandez M, eds. Functional Imaging and Modeling of the Heart. Barcelona, Spain: Springer; 434-445, 2005.

Elhendy A, Mahoney DW, Khandheria BK, Paterick TE, Burger KN, Pellikka PA. Prognostic significance of the location of wall motion abnormalities during exercise echocardiography. J Am Coll Cardiol, 40:1623-1629, 2002.

Geary GG, Smith GT, McNamara JJ. Defining the anatomic perfusion bed of an occluded coronary artery and the region at risk to infarction: a comparative study in the baboon, pig and dog. Am J Cardiol, 47:1240-1247, 1981.

George I, Cheng Y, Yi GH, He KL, Li X, Oz MC, Holmes J, Wang J. Effect of passive cardiac containment on ventricular synchrony and cardiac function in awake dogs. Eur J Cardiothorac Surg, 31:55-64, 2007.

George I, Cheng Y, Yi GH, Reiken S, Gu A, Tao YK, Muraskin J, Qin S, He KL, Hay I, Yu K, Oz MC, Burkhoff D, Holmes J, Wang J. Bradycardic Therapy Improves Left Ventricular Function and Remodeling in Dogs with Coronary Embolization-Induced Chronic Heart Failure. J Pharmacol Exp Ther, 2007.

Gill RM, Jones BD, Corbly AK, Ohad DG, Smith GD, Sandusky GE, Christe ME, Wang J, Shen W. Exhaustion of the Frank-Starling mechanism in conscious dogs with heart failure induced by chronic coronary microembolization. Life Sci, 79:536-44, 2006.

Gill RM, Jones BD, Corbly AK, Wang J, Braz JC, Sandusky GE, Shen W. Cardiac diastolic dysfunction in conscious dogs with heart failure induced by chronic coronary microembolization. Am J Physiol Heart Circ Physiol, 291:H3154-8, 2006.

Gorman JH, 3rd, Gorman RC, Plappert T, Jackson BM, Hiramatsu Y, St John-Sutton MG, Edmunds LH, Jr. Infarct size and location determine development of mitral regurgitation in the sheep model. J Thorac Cardiovasc Surg, 115:615-22, 1998.

Guccione JM, Waldman LK, McCulloch AD, Mechanics of active contraction in cardiac muscle: Part II—Cylindrical models of the systolic left ventricle, J Biomech Eng 115 (1993) 82-90.

Harken AH, Simson MB, Haselgrove J, Wetstein L, Harden WR, Barlow CH. Early ischemia after complete coronary ligation in the rabbit, dog, pig, and monkey. Am J Physiol Heart Circ Physiol, 241:H202-H210, 1981.

Hashima AR, Young AA, McCulloch AD, Waldman LK. Nonhomogeneous analysis of epicardial strain distributions during acute myocardial ischemia in the dog. J Biomech, 26:19-35, 1993.

Heimdal A, Stoylen A, Torp H, Skjaerpe T. Real-time strain rate imaging of the left ventricle by ultrasound. J Am Soc Echocardiogr, 11:1013-9, 1998.

Heller EN, Staib LH, Dione DP, Constable RT, Shi CQ, Duncan JS, Sinusas AJ. A new method for quantification of spatial and temporal parameters of endocardial motion: evaluation of experimental infarction using magnetic resonance imaging. Can J Cardiol, 17:309-18, 2001.

Herz SL, et al., "Model-Based Screening of Wall Motion Measures for Detection of Ischemia in Three-Dimensional Cardiac Images," Computer Methods in Applied Mechanics and Engineering, Jun. 15, 2007.

Herz SL, Ingrassia CM, Costa KD, Homma S, Holmes JW. Detection of regional ischemia by four-dimensional wall motion analysis (abstract). European Society of Biomechanics. 's-Hertogenbosch, Netherlands, 2004.

Herz SL, Ingrassia CM, Homma S, Costa KD, Holmes JW. Parameterization of left ventricular wall motion for detection of regional ischemia. Ann Biomed Eng, 33:912-919, 2005.

Herz SL, Pulerwitz TC, Abe Y, Okajima K, Laine AF, Di Tullio MR, Homma S, Holmes JW. A novel quantitative three-dimensional wall motion analysis of contrast enhanced real-time three dimensional dobutamine stress echocardiography (abstract). J Am Soc Echocardiogr, 19:639, 2006.

Herz SL, Pulerwitz TC, Laine AF, Hirata K, DiTullio MR, Homma S, Holmes JW. Novel technique for quantitative wall motion analysis using three-dimensional echocardiography (abstract). American Society of Echocardiography. San Diego, CA, 2004.

Hillenbrand HB, Lima JA, Bluemke DA, Beache GM, McVeigh ER. Assessment of myocardial systolic function by tagged magnetic resonance imaging. J Cardiovasc Magn Reson, 2:57-66, 2000.

Holmes JW, Borg TK, Covell JW. Structure and mechanics of healing myocardial infarcts. Annu Rev Biomed Eng, 7:223-253, 2005.

Holmes JW, Covell JW. Collagen fiber orientation in myocardial scar tissue. Cardiovasc Pathobiol, 1:15-22, 1996.

Holmes JW, Nunez JA, Covell JW. Functional implications of myocardial scar structure. Am J Physiol Heart Circ Physiol, 272:H2123-30, 1997.

Holmes JW, Takayama Y, LeGrice I, Covell JW, Depressed regional deformation near anterior papillary muscle, Am J Physiol 269 (1995) H262-270.

Holmes JW, Yamashita H, Waldman LK, Covell JW. Scar remodeling and transmural deformation after infarction in the pig. Circulation, 90:411-20, 1994.

Horn BKP, Schunck BG. Determining optical flow. Artificial Intelligence, 17, 1981.

Hunt SA, al. e. ACC/AHA 2005 Guideline update for the diagnosis and management of chronic heart failure in the adult—summary article. JACC, 46:1116-1143, 2005.

Hunter PJ, Smaill BH. The analysis of cardiac function: a continuum approach. Prog Biophys Molec Biol, 52:101-164, 1988.

Ingrassia CM, Herz SL, Costa KD, Holmes JW. Impact of ischemic region size on regional wall motion (abstract). 2003 Annual Fall Meeting Biomedical Engineering Society. Nashville, TN, 2003.

Ingrassia CM, Herz SL, Homma S, Costa KD, Holmes JW. Analysis of regional cardiac dynamics using a 4D representation of the LV endocardium (abstract). Biomedical Engineering Society 2005. Baltimore, MD, 2005.

Ingrassia CM, Usyk TP, Kerckhoffs RCP, McCulloch AD, Costa KD, Holmes JW. Model-based development of 4-dimensional wall motion measures. Comp Meth Appl Mech Eng, in press.

Kass DA, Cardiac resynchronization therapy, J Cardiovasc Electrophysiol 16 Suppl 1 (2005) S35-41.

Katz WE, Gulati VK, Mahler CM, Gorcsan J, 3rd. Quantitative evaluation of the segmental left ventricular response to dobutamine stress by tissue Doppler echocardiography. Am J Cardiol, 79:1036-42, 1997.

Konofagou EE, D'Hooge J, Ophir J. Myocardial elastography—a feasibility study in vivo. Ultrasound Med Biol, 28:475-82, 2002.

Kowallik P, Schulz R, Guth BD, Schade A, Paffhausen W, Gross R, Heusch G. Measurement of regional myocardial blood flow with multiple colored microspheres. Circulation, 83:974-82, 1991.

Kraitchman DL, Sampath S, Castillo E, Derbyshire JA, Boston RC, Bluemke DA, Gerber BL, Prince JL, Osman NF. Quantitative ischemia detection during cardiac magnetic resonance stress testing by use of FastHARP. Circulation, 107:2025-30, 2003.

Lang RM, Bierig M, Devereux RB, Flachskampf FA, Foster E, Pellikka PA, Picard MH, Roman MJ, Seward J, Shanewise JS, Solomon SD, Spencer KT, Sutton MS, Stewart WJ. Recommendations for chamber quantification: a report from the American Society of Echocardiography's Guidelines and Standards Committee and the Chamber Quantification Writing Group, developed in conjunction with the European Association of Echocardiography, a branch of the European Society of Cardiology. J Am Soc Echocardiogr, 18:1440-63, 2005.

Lavine SJ. Prediction of heart failure post myocardial infarction: comparison of ejection fraction, transmitral filling parameters, and the index of myocardial performance. Echocardiography, 20:691-701, 2003.

Legrice IJ, Hunter PJ, Smaill BH, Laminar structure of the heart: a mathematical model, Am J Physiol 272 (1997) H2466-2476.

Matsumura Y, Hozumi T, Arai K, Sugioka K, Ujino K, Takemoto Y, Yamagishi H, Yoshiyama M, Yoshikawa J. Non-invasive assessment of myocardial ischaemia using new real-time three-dimensional dobutamine stress echocardiography: comparison with conventional two-dimensional methods. Eur Heart J, 26:1625-32, 2005.

Mazhari R, McCulloch AD. Integrative models for understanding the structural basis of regional mechanical dysfunction in ischemic myocardium. Ann Biomed Eng, 28:979-990, 2000.

Mazhari R, Omens JH, Covell JW, McCulloch AD. Structural basis of regional dysfunction in acutely ischemic myocardium. Cardiovasc Res, 47:284-293, 2000.

Mikic I, Krucinski S, Thomas JD. Segmentation and tracking in echocardiographic sequences: active contours guided by optical flow estimates. IEEE Trans Med Imaging, 17:274-84, 1998.

Mohri S, He KL, Dickstein M, Mika Y, Shimizu J, Shemer I, Yi GH, Wang J, Ben-Haim S, Burkhoff D. Cardiac contractility modulation by electric currents applied during the refractory period. Am J Physiol Heart Circ Physiol, 282:H1642-7, 2002.

Moller JE, Hillis GS, Oh JK, Reeder GS, Gersh BJ, Pellikka PA. Wall motion score index and ejection fraction for risk stratification after acute myocardial infarction. Am Heart J, 151:419-25, 2006.

Moynihan PF, Parisi AF, Feldman CL. Quantitative detection of regional left ventricular contraction abnormalities by two-dimensional echocardiography. I. Analysis of methods. Circulation, 63:752-60, 1981.

Nielsen PM, Le Grice IJ, Smaill BH, Hunter PJ, Mathematical model of geometry and fibrous structure of the heart, Am J Physiol 260 (1991) H1365-1378.

O'Boyle JE, Parisi AF, Nieminen M, Kloner RA, Khuri S. Quantitative detection of regional left ventricular contraction abnormalities by 2-dimensional echocardiography. Comparison of myocardial thickening and thinning and endocardial motion in a canine model. Am J Cardiol, 51:1732-8, 1983.

Paetsch I, Jahnke C, Wahl A, Gebker R, Neuss M, Fleck E, Nagel E. Comparison of dobutamine stress magnetic resonance, adenosine stress magnetic resonance, and adenosine stress magnetic resonance perfusion. Circulation, 110:835-42, 2004.

Papademetris X, Sinusas AJ, Dione DP, Duncan JS. Estimation of 3D left ventricular deformation from echocardiography. Med Image Anal, 5:17-28, 2001.

Pearlman JD, Hogan RD, Wiske PS, Franklin TD, Weyman AE. Echocardiographic definition of the left ventricular centroid. I. Analysis of methods for centroid calculation from a single tomogram. J Am Coll Cardiol, 16:986-992, 1990.

Pellikka PA. Stress echocardiography for the diagnosis of coronary artery disease: progress towards quantification. Curr Opin Cardiol, 20:395-8, 2005.

Pham DL, Xu C, Prince JL. Current methods in medical image segmentation. Annu Rev Biomed Eng, 2:315-37, 2000.

Pulerwitz T, Hirata K, Abe Y, Otsuka R, Herz S, Okajima K, Jin Z, Di Tullio MR, Homma S. Feasibility of using a real-time 3-dimensional technique for contrast dobutamine stress echocardiography. J Am Soc Echocardiogr, 19:540-5, 2006.

Reiber JH, van der Zwet PM, Koning G, von Land CD, van Meurs B, Gerbrands JJ, Buis B, van Voorthuisen AE. Accuracy and precision of quantitative digital coronary arteriography: observer-, short-, and medium-term variabilities. Cathet Cardiovasc Diagn, 28:187-98, 1993.

Roethy W, Fiehn E, Suehiro K, Gu A, Yi GH, Shimizu J, Wang J, Zhang G, Ranieri J, Akella R, Funk SE, Sage EH, Benedict J, Burkhoff D. A growth factor mixture that significantly enhances angiogenesis in vivo. J Pharmacol Exp Ther, 299:494-500, 2001.

Sampath S, Derbyshire JA, Atalar E, Osman NF, Prince JL. Real-time imaging of two-dimensional cardiac strain using a harmonic phase magnetic resonance imaging (HARP-MRI) pulse sequence. Magn Reson Med, 50:154-63, 2003.

Sawada SG, Segar DS, Ryan T, Brown SE, Dohan AM, Williams R, Fineberg NS, Armstrong WF, Feigenbaum H. Echocardiographic detection of coronary artery disease during dobutamine infusion. Circulation, 83:1605-14, 1991.

Schiller NB, Shah PM, Crawford M, DeMaria A, Devereux R, Feigenbaum H, Gutgesell H, Reichek N, Sahn D, Schnittger I, et al. Recommendations for quantitation of the left ventricle by two-dimensional echocardiography. American Society of Echocardiography Committee on Standards, Subcommittee on Quantitation of Two-Dimensional Echocardiograms. J Am Soc Echocardiogr, 2:358-367, 1989.

Schoenhagen P, Nissen SE. Assessing coronary plaque burden and plaque vulnerability: atherosclerosis imaging with IVUS and emerging noninvasive modalities. Am Heart Hosp J, 1:164-9, 2003.

Schuijf JD, Shaw LJ, Wijns W, Lamb HJ, Poldermans D, de Roos A, van der Wall EE, Bax JJ. Cardiac imaging in coronary artery disease: differing modalities. Heart, 91:1110-7, 2005.

Shekhar R, Zagrodsky V, Garcia MJ, Thomas JD. Registration of real-time 3-D ultrasound images of the heart for novel 3-D stress echocardiography. IEEE Trans Med Imaging, 23:1141-9, 2004.

Sinusas AJ, Papademetris X, Constable RT, Dione DP, Slade MD, Shi P, Duncan JS. Quantification of 3-D regional myocardial deformation: shape-based analysis of magnetic resonance images. Am J Physiol Heart Circ Physiol, 281:H698-714, 2001.

Stoylen A, Heimdal A, Bjornstad K, Wiseth R, Vik-Mo H, Torp H, Angelsen B, Skjaerpe T. Strain rate imaging by ultrasonography in the diagnosis of coronary artery disease. J Am Soc Echocardiogr, 13:1053-64, 2000.

Sutherland GR, Stewart MJ, Groundstroem KW, Moran CM, Fleming A, Guell-Peris FJ, Riemersma RA, Fenn LN, Fox KA, McDicken WN. Color Doppler myocardial imaging: a new technique for the assessment of myocardial function. J Am Soc Echocardiogr, 7:441-58, 1994.

Takayama Y, Holmes JW, LeGrice I, Covell JW, Enhanced regional deformation at the anterior papillary muscle insertion site after chordal transsection, Circulation 93 (1996) 585-593.

Takuma S, Ota T, Muro T, Hozumi T, Sciacca R, Di Tullio MR, Blood DK, Yoshikawa J, Homma S. Assessment of left ventricular function by real-time 3-dimensional echocardiography compared with conventional noninvasive methods. J Am Soc Echocardiogr, 14:275-84, 2001.

Takuma S, Zwas DR, Fard A, Wu H, Chaudhry H, Di Tullio MR, Ota T, Homma S. Real-time, 3-dimensional echocardiography acquires all standard 2-dimensional images from 2 volume sets: a clinical demonstration in 45 patients. J Am Soc Echocardiogr, 12:1-6, 1999.

Theroux P, Franklin D., Ross Jr, J. Kemper WS, Regional myocardial function during acute coronary artery occlusion and its modification by pharmacologic agents in the dog, Circ Res 35 (1974) 896-908.

Theroux P, Ross Jr J, Franklin D, Covell JW, Bloor CM, Sasayama S. Regional myocardial function and dimensions early and late after myocardial infarction in the unanesthetized dog. Circ Res, 40:158-165, 1977.

Tobis JM, Mallery J, Mahon D, Lehmann K, Zalesky P, Griffith J, Gessert J, Moriuchi M, McRae M, Dwyer ML, et al. Intravascular ultrasound imaging of human coronary arteries in vivo. Analysis of tissue characterizations with comparison to in vitro histological specimens. Circulation, 83:913-26, 1991.

Tyberg JV, Forrester JS, Wyatt HL, Goldner SJ, Parmley WW, Swan HJC. An analysis of segmental ischemic dysfunction using the pressure-length loop. Circulation, 49:748-754, 1974.

Usyk TP, Le Grice IJ, McCulloch AD, Computational model of three-dimensional cardiac electromechanics, Computing and Visualization in Science 4 (2002) 249-257.

Usyk TP, Mazhari R, McCulloch AD, Effect of laminar orthotropic myofiber architecture on regional stress and strain in the canine left ventricle, Journal of Elasticity 61 (2000) 143-164.

Usyk TP, McCulloch AD. Electromechanical model of cardiac resynchronization in the dilated failing heart with left bundle branch block. J Electrocardiol, 36 Suppl:57-61, 2003.

Usyk TP, McCulloch AD. Relationship between regional shortening and asynchronous electrical activation in a three-dimensional model of ventricular electromechanics. J Cardiovasc Electrophysiol, 14:S196-202, 2003.

Villarreal FJ, Lew WYW, Waldman LK, Covell JW. Transmural myocardial deformation in the ischemic canine left ventricle. Circ Res, 68:368-381, 1991.

von Ramm OT, Smith SW. Real time volumetric ultrasound imaging system. J Digit Imaging, 3:261-6, 1990.

Waldman LK, Fung YC, Covell JW, Transmural myocardial deformation in the canine left ventricle. Normal in vivo three-dimensional finite strains, Circ Res 57 (1985) 152-163.

Wilkins GT, Southern JF, Choong CY, Thomas JD, Fallon JT, Guyer DE, Weyman AE. Correlation between echocardiographic endocardial surface mapping of abnormal wall motion and pathologic infarct size in autopsied hearts. Circulation, 77:978-87, 1988.

Wiske PS, Pearlman JD, Hogan RD, Franklin TD, Weyman AE. Echocardiographic definition of the left ventricular centroid. II. Determination of the optimal centroid during systole in normal and infarcted hearts. J Am Coll Cardiol, 16:993-999, 1990.

Workman Jr. J, Mark H. Comparison of goodness of fit statistics for linear regression, part III. Spectroscopy, 19:1-3, 2004.

Wyman BT, Hunter WC, Prinzen FW, McVeigh ER, Mapping propagation of mechanical activation in the paced heart with MRI tagging, Am J Physiol 276 (1999) H881-891.

Yao SS, Qureshi E, Syed A, Chaudhry FA. Novel stress echocardiographic model incorporating the extent and severity of wall motion abnormality for risk stratification and prognosis. Am J Cardiol, 94:715-9, 2004.

Young AA, Axel L, Dougherty L, Bogen DK, Parenteau CS. Validation of tagging with MR imaging to estimate material deformation. Radiology, 188:101-8, 1993.

Young AA, Hunter PJ, Smaill BH, Estimation of epicardial strain using the motions of coronary bifurcations in biplane cineangiography, IEEE Trans Biomed Eng 39 (1992) 526-531.

Young AA, Imai H, Chang CN, Axel L. Two-dimensional left ventricular deformation during systole using magnetic resonance imaging with spatial modulation of magnetization. Circulation, 89:740-52, 1994.

Zimmerman SD, Karlon WJ, Holmes JW, Omens JH, Covell JW. Structural and mechanical factors influencing infarct scar collagen organization. Am J Physiol Heart Circ Physiol, 278:H194-H200, 2000.

Zwas DR, Takuma S, S. M-J, Fard A, Chaudry H, Wu H, Di Tullio MR, Homma S. Feasibility of real-time 3-dimensional treadmill stress echocardiography. J Am Soc Echocardiogr, 12:285-289, 1999.

BiV  LBBB

METHODS FOR PROVIDING DIAGNOSTIC INFORMATION USING ENDOCARDIAL SURFACE DATA FOR A PATIENT'S HEART

CROSS-REFERENCE TO RELATED APPLICATIONS

This application claims the benefit under 35 U.S.C. §119 (e) of U.S. Patent Application Nos. 60/799,460, filed May 11, 2006, and 60/802,942, filed May 23, 2006, which are both hereby incorporated by reference herein in their entireties.

STATEMENT REGARDING FEDERALLY SPONSORED RESEARCH OR DEVELOPMENT

The government may have certain rights in the claimed subject matter pursuant to a grant from the National Science Foundation, Award No. BES-02-01617.

BACKGROUND

Biomedical imaging is a dynamic and rapidly expanding field. Technologies for imaging both anatomy and function of organs throughout the body continue to emerge, and existing technologies continue to benefit from increases in resolution and speed. Because cardiovascular disease causes numerous deaths in the United States, cardiac imaging has been a natural focus for new developments in imaging technology. Technology for imaging all aspects of heart anatomy and function has advanced dramatically in recent years. However, the ability to acquire image data using cardiac imaging technology has outpaced the ability to analyze and interpret the acquired data.

SUMMARY

Methods for providing diagnostic information using endocardial surface data for a patient's heart are provided.

In some embodiments, methods for providing diagnostic information using endocardial surface data for a patient's heart include receiving endocardial surface data for the left ventricle of a heart that represents the endocardial surface of the left ventricle at multiple times over a heartbeat, including end diastole and end systole of the heartbeat. The endocardial surface data is obtained using a volumetric imaging application. A representation in prolate spheroidal coordinates of the endocardial surface of the left ventricle at end diastole and end systole is generated using the endocardial surface data. The prolate spheroidal coordinates include a longitudinal angular coordinate $\mu$, a circumferential angular coordinate $\theta$, and a coordinate $\lambda$ as a function of longitudinal angular coordinate $\mu$ and circumferential angular coordinate $\theta$. $\lambda_{ED}$ represents the value of coordinate $\lambda$ at end diastole, and $\lambda_{ES}$ represents the value of coordinate $\lambda$ at end systole. Three-dimensional fractional shortening ("3DFS") of the left ventricle is computed as $3DFS=(\lambda_{ED}-\lambda_{ES})/\lambda_{ED}$. The three-dimensional fractional shortening identifies an ischemic region of the left ventricle.

In one example, an indication of the three-dimensional fractional shortening is provided on a map of the left ventricle, such that the ischemic region of the left ventricle is identified on the map.

In some embodiments, methods for providing diagnostic information using endocardial surface data for a patient's heart include receiving endocardial surface data for the left ventricle of a heart that represents the endocardial surface of the left ventricle at multiple times over a heartbeat. The endocardial surface data is obtained using a volumetric imaging application. A representation in prolate spheroidal coordinates of the endocardial surface of the left ventricle at least a portion of the multiple times is generated using the endocardial surface data. The prolate spheroidal coordinates include a longitudinal angular coordinate $\mu$, a circumferential angular coordinate $\theta$, and a coordinate $\lambda$ as a function of longitudinal angular coordinate $\mu$ and circumferential angular coordinate $\theta$. A measure that provides diagnostic information related to the left ventricle is computed based at least on part on the value of coordinate $\lambda$ at the at least a portion of the multiple times.

In one example, an indication of the measure is provided on a map of the left ventricle. The map can include an area-preserving map of the left ventricle, a circumferential polar plot of the left ventricle, or any other suitable map of the left ventricle. In another example, the measure is provided to a mapping application, such that an indication of the measure can be provided on a map of the left ventricle by the mapping application.

In yet another example, the multiple times over the heartbeat represented by the endocardial surface data include end diastole of the heartbeat. In still another example, the multiple times over the heartbeat represented by the endocardial surface data include end diastole and end systole of the heartbeat.

In still another example, the volumetric imaging application can include real-time three-dimensional echocardiography, magnetic resonance imaging, x-ray ventriculography, computed tomography, or any other suitable volumetric imaging application.

In yet another example, the endocardial surface data is converted into the prolate spheroidal coordinates. The prolate spheroidal coordinates are fitted to a finite element mesh representing the endocardial surface of left ventricle. The finite element mesh can be constructed from, for example, polynomial basis functions.

In yet another example, the endocardial surface data for the left ventricle of the heart corresponds to spatial coordinates in a spatial coordinate system defining the endocardial surface of the left ventricle. In such an example, generating a representation in prolate spheroidal coordinates of the endocardial surface of the left ventricle includes converting the spatial coordinates in the spatial coordinate system to Cartesian coordinates $X_1$, $X_2$, and $X_3$ in a Cartesian coordinate system, and converting Cartesian coordinates $X_1$, $X_2$, and $X_3$ to the prolate spheroidal coordinates.

In still another example, the endocardial surface data for the left ventricle of the heart corresponds to Cartesian coordinates $X_1$, $X_2$, and $X_3$ defining the endocardial surface of the left ventricle. In such an example, generating a representation in prolate spheroidal coordinates of the endocardial surface of the left ventricle includes converting Cartesian coordinates $X_1$, $X_2$, and $X_3$ to the prolate spheroidal coordinates. The prolate spheroidal coordinates can be defined by, for example, transformation equations $X_1 = d \cdot \cos h\lambda \cdot \cos \mu$, $X_2 = d \cdot \sin h\lambda \cdot \sin \mu \cdot \cos \theta$, and $X_3 = d \cdot \sin h\lambda \cdot \sin \mu \cdot \sin \theta$, in which the variable d is a focal length of the prolate spheroidal representation.

In yet another example, the multiple times over the heartbeat represented by the endocardial surface data include end diastole and end systole of the heartbeat. In such an example, a representation in prolate spheroidal coordinates of the endocardial surface of the left ventricle can be generated at end diastole and end systole, such that $\lambda_{ED}$ represents the value of coordinate $\lambda$ at end diastole and $\lambda_{ES}$ represents the value of coordinate $\lambda$ at end systole. In such an example, three-dimensional fractional shortening ("3DFS") of the left ventricle can be computed as $3DFS=(\lambda_{ED}-\lambda_{ES})/\lambda_{ED}$.

In still another example, the multiple times over the heartbeat represented by the endocardial surface data include end diastole of the heartbeat. In such an example, a representation in prolate spheroidal coordinates of the endocardial surface of the left ventricle can be generated at end diastole and two or more additional times, such that $\lambda_{ED}$ represents the value of coordinate $\lambda$ at end diastole and $\lambda_{MIN}$ represents the minimum value of coordinate $\lambda$ over the heartbeat. In such an example, four-dimensional fractional shortening ("4DFS") of the left ventricle can be computed as 4DFS=$(\lambda_{ED}-\lambda_{MIN})/\lambda_{ED}$. The minimum value of coordinate $\lambda$ over the heartbeat $\lambda_{MIN}$ can be determined by, for example, fitting the prolate spheroidal coordinates to a finite element mesh representing the endocardial surface of the left ventricle.

In yet another example, the measure can be a derivative of coordinate $\lambda$ such as $\partial\lambda/\partial\mu$, $\partial\lambda/\partial\theta$, $\partial\lambda/\partial t$, $\partial^2\lambda/\partial\mu\partial t$, or $\partial^2\lambda/\partial\theta\partial t$. In still another example, the measure can be maximum systolic $\partial\lambda/\partial t$ for the heartbeat.

In yet another example, the diagnostic information related to the left ventricle can be an indication of size, location, or severity of one or more ischemic regions of the left ventricle, synchrony of contraction of the left ventricle, or any other suitable diagnostic information related to the left ventricle.

In some embodiments, a computer readable medium storing computer executable instructions for providing diagnostic information using endocardial surface data for a patient's heart is provided. The executable instructions include generating a representation in prolate spheroidal coordinates of the endocardial surface of the left ventricle of a heart at multiple times over a heartbeat using endocardial surface data. The endocardial surface data is obtained using a volumetric imaging application. The prolate spheroidal coordinates include a longitudinal angular coordinate $\mu$, a circumferential angular coordinate $\theta$, and a coordinate $\lambda$ as a function of longitudinal angular coordinate $\mu$ and circumferential angular coordinate $\theta$. The executable instructions include computing a measure based at least on part on the value of coordinate $\lambda$ at the multiple times, the measure providing diagnostic information related to the left ventricle.

In some embodiments, methods for providing diagnostic information using endocardial surface data for a patient's heart include receiving endocardial surface data for the left ventricle of a heart that represents the endocardial surface of the left ventricle at multiple times over a heartbeat. The endocardial surface data is obtained using a volumetric imaging application. A three-dimensional representation of the endocardial surface of the left ventricle at at least a portion of the multiple times is generated using the endocardial surface data. The three-dimensional representation includes a coordinate $\lambda$ that identifies a position of the endocardial surface with respect to a central axis of the left ventricle. A measure that provides diagnostic information related to the left ventricle is computed based at least in part on the value of coordinate $\lambda$ at the at least a portion of the multiple times.

In one example, the three-dimensional representation of the endocardial surface is generated in prolate spheroidal coordinates that include a longitudinal angular coordinate $\mu$, a circumferential angular coordinate $\theta$, and the coordinate $\lambda$ as a function of longitudinal angular coordinate $\mu$ and circumferential angular coordinate $\theta$.

In another example, the multiple times over the heartbeat represented by the endocardial surface data include end diastole and end systole of the heartbeat. In such an example, a three-dimensional representation of the endocardial surface of the left ventricle can be generated at end diastole and end systole, such that $\lambda_{ED}$ represents the value of coordinate $\lambda$ at end diastole and $\lambda_{ES}$ represents the value of coordinate $\lambda$ at end systole. In such an example, three-dimensional fractional shortening ("3DFS") of the left ventricle can be computed as 3DFS=$(\lambda_{ED}-\lambda_{ES})/\lambda_{ED}$.

In yet another example, the multiple times over the heartbeat represented by the endocardial surface data include end diastole of the heartbeat. In such an example, a three-dimensional representation of the endocardial surface of the left ventricle can be generated at end diastole and two or more additional times over the heartbeat, such that $\lambda_{ED}$ represents the value of coordinate $\lambda$ at end diastole and $\lambda_{MIN}$ represents the minimum value of coordinate $\lambda$ over the heartbeat. In such an example, four-dimensional fractional shortening ("4DFS") of the left ventricle can be computed as 4DFS=$(\lambda_{ED}-\lambda_{MIN})/\lambda_{ED}$.

DETAILED DESCRIPTION

Methods for providing diagnostic information using endocardial surface data for a patient's heart are provided.

Technology for volumetric imaging of the heart has advanced dramatically in recent years. However, the ability to acquire image data using cardiac imaging technology has outpaced the ability to analyze and interpret the acquired data. Methods for providing diagnostic information using endocardial surface data for a patient's heart described herein can use, for example, data obtained with a volumetric imaging application in order to provide such diagnostic information. Data can be extracted from a large dataset received from a volumetric imaging application and reduced to a quantitative, diagnostically useful measure. The measure can be presented in a simple, straightforward way to a clinician.

In some embodiments, for example, the data received from a volumetric imaging application is endocardial surface data for the left ventricle of a heart. Using the endocardial surface data, a representation of the endocardial surface of the left ventricle is generated. For example, the representation can be in prolate spheroidal coordinates ($\mu$, $\theta$, $\lambda$). A quantitative, diagnostically useful measure is computed based on the representation of the endocardial surface. For example, the measure can be based at least in part on the value of prolate spheroidal coordinate $\lambda$. The measure can provide information related to, for example, an ischemic region of the left ventricle, synchrony of contraction of the left ventricle, or any other measure that is useful to a clinician. The measure can be provided on a map of the left ventricle for presentation to the clinician. Alternatively, the measure can be provided to a separate mapping application for presentation to the clinician.

Figure 1:
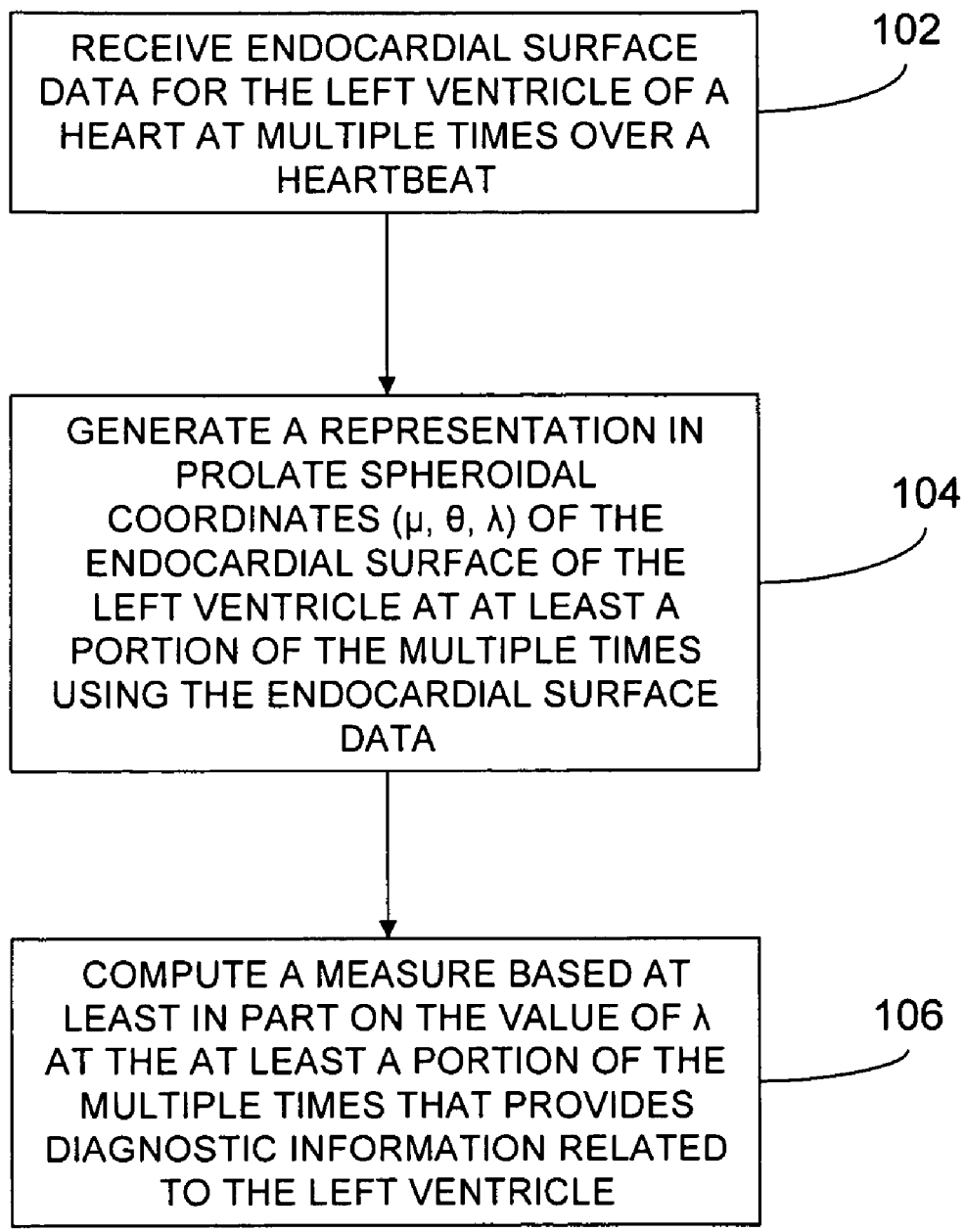
FIG. 1 is an illustrative diagram demonstrating a method for providing diagnostic information using endocardial surface data for the left ventricle of a heart in accordance with some embodiments of the disclosed subject matter.

FIG. 1 is an illustrative diagram demonstrating a method for providing diagnostic information using endocardial surface data for a heart in accordance with some embodiments of the disclosed subject matter. Endocardial surface data for the left ventricle of a heart is received (102 in FIG. 1). The endocardial surface data represents the endocardial surface of the left ventricle of the heart at multiple times over a heartbeat. By representing the endocardial surface of the left ventricle at multiple times, the endocardial surface data is indicative of left ventricular wall motion. For example, the endocardial surface can be represented at any number of times over the heartbeat, including when the left ventricle has fully expanded and is ready to contract (i.e., end diastole), when the left ventricle has finished contracting (i.e., end systole), or any other time over the heartbeat. The endocardial surface data can be obtained using a volumetric imaging application. For example, the endocardial surface data can be obtained using real-time three-dimensional echocardiography, magnetic resonance imaging, x-ray ventriculography, computed tomography, or any other suitable volumetric imaging application. The endocardial surface data can represent the endocardial surface of the left ventricle at any suitable number of times. Such number can be based on, for example, the number of times over a heartbeat that the volumetric imaging application captures an image of the left ventricle of the heart. Based on current volumetric imaging methods, this number may be, for example, ten to fifteen times over a heartbeat. However, the endocardial surface data obtained from the volumetric imaging application can represent the endocardial surface at any suitable number of times over a heartbeat, and the methods described herein can be used in conjunction with any such volumetric imaging application.

A representation in prolate spheroidal coordinates of the endocardial surface of the left ventricle at least a portion of the multiple times is generated using the endocardial surface data (104 in FIG. 1). For example, a representation in prolate spheroidal coordinates can be generated at one, some, or all of the multiple times over the heartbeat for which data was received. The prolate spheroidal coordinates can include a longitudinal angular coordinate $\mu$, a circumferential angular coordinate $\theta$, and a coordinate $\lambda$ as a function of longitudinal angular coordinate $\mu$ and circumferential angular coordinate $\theta$. In some embodiments, the representation can be generated by converting the endocardial surface data into the prolate spheroidal coordinates, and fitting the prolate spheroidal coordinates to a finite element mesh representing the endocardial surface. It should be noted that while the embodiments herein are described in connection with a prolate spheroidal coordinate system, one of ordinary skill in the art will recognize that the representation of the endocardial surface can be generated in any suitable three-dimensional coordinate system.

A measure is computed that is based at least in part on the value of coordinate $\lambda$ at the at least a portion of the multiple times and that provides diagnostic information related to the left ventricle (106 in FIG. 1). The diagnostic information related to the left ventricle provided by the measure can include, for example, an indication of size of one or more ischemic regions of the left ventricle, location of one or more ischemic regions of the left ventricle, severity of one or more ischemic regions of the left ventricle, synchrony of contraction of the left ventricle, or any other suitable diagnostic information related to the left ventricle.

In one example, an indication of the measure can be provided on a map of the left ventricle. The map can be, for example, an area-preserving map of the left ventricle, a circumferential plot of the left ventricle, or any other suitable map of the left ventricle. In another example, the measure can be provided to a mapping application such that an indication of the measure can be provided on a map of the left ventricle by the mapping application. For example, the measure can be provided to a mapping application separate from the application that computes the measure in accordance with the methods described herein.

Figure 2:
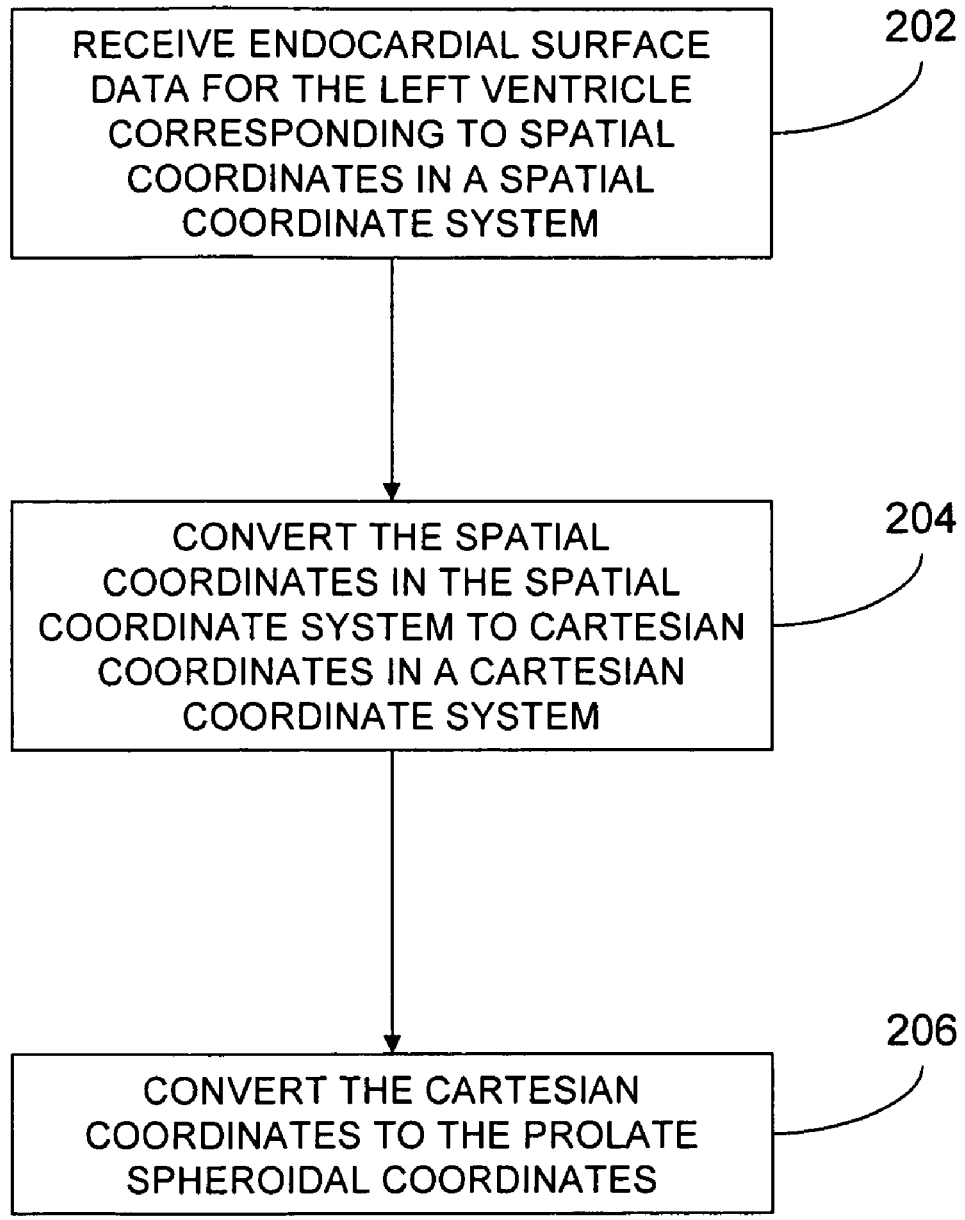
FIG. 2 is an illustrative diagram demonstrating a method for converting endocardial surface data to prolate spheroidal coordinates in accordance with some embodiments of the disclosed subject matter.

FIG. 2 is an illustrative diagram demonstrating a method for converting endocardial surface data to prolate spheroidal coordinates in accordance with some embodiments of the disclosed subject matter. The method described in FIG. 2 can be performed, for example, in connection with generating a representation in prolate spheroidal coordinates of the endocardial surface of the left ventricle (104 in FIG. 1). Endocardial surface data for the left ventricle corresponding to spatial coordinates in a spatial coordinate system is received (202 in FIG. 2). The endocardial surface data as obtained using the volumetric imaging application can be in, for example, any spatial coordinate system. In the event that the spatial coordinate system is a non-Cartesian coordinate system, the spatial coordinates are converted to Cartesian coordinates $X_1$, $X_2$, and $X_3$ in a Cartesian coordinate system (204 in FIG. 2). Cartesian coordinates $X_1$, $X_2$, and $X_3$ are converted to the prolate spheroidal coordinates (206 in FIG. 2). The prolate spheroidal coordinates can be defined by, for example, the following transformation equations, in which the variable d comprises a focal length of the prolate spheroidal representation:

$$X_1 = d \cdot \cos h\lambda \cdot \cos \mu \quad (1)$$

$$X_2 = d \cdot \sin h\lambda \cdot \sin \mu \cdot \cos \theta \quad (2)$$

$$X_3 = d \cdot \sin h\lambda \cdot \sin \mu \cdot \sin \theta \quad (3)$$

The method for converting endocardial surface data to prolate spheroidal coordinates described in connection with FIG. 2 is merely illustrative, and it should be noted that endocardial surface data can alternatively be received in Cartesian coordinates. In such an example, the conversion of the spatial coordinates to Cartesian coordinates (204 of FIG. 2) would be unnecessary. In another example, spatial coordinates in a non-Cartesian coordinate system can be received and converted directly to prolate spheroidal coordinates using suitable transformation equations.

Figure 3:
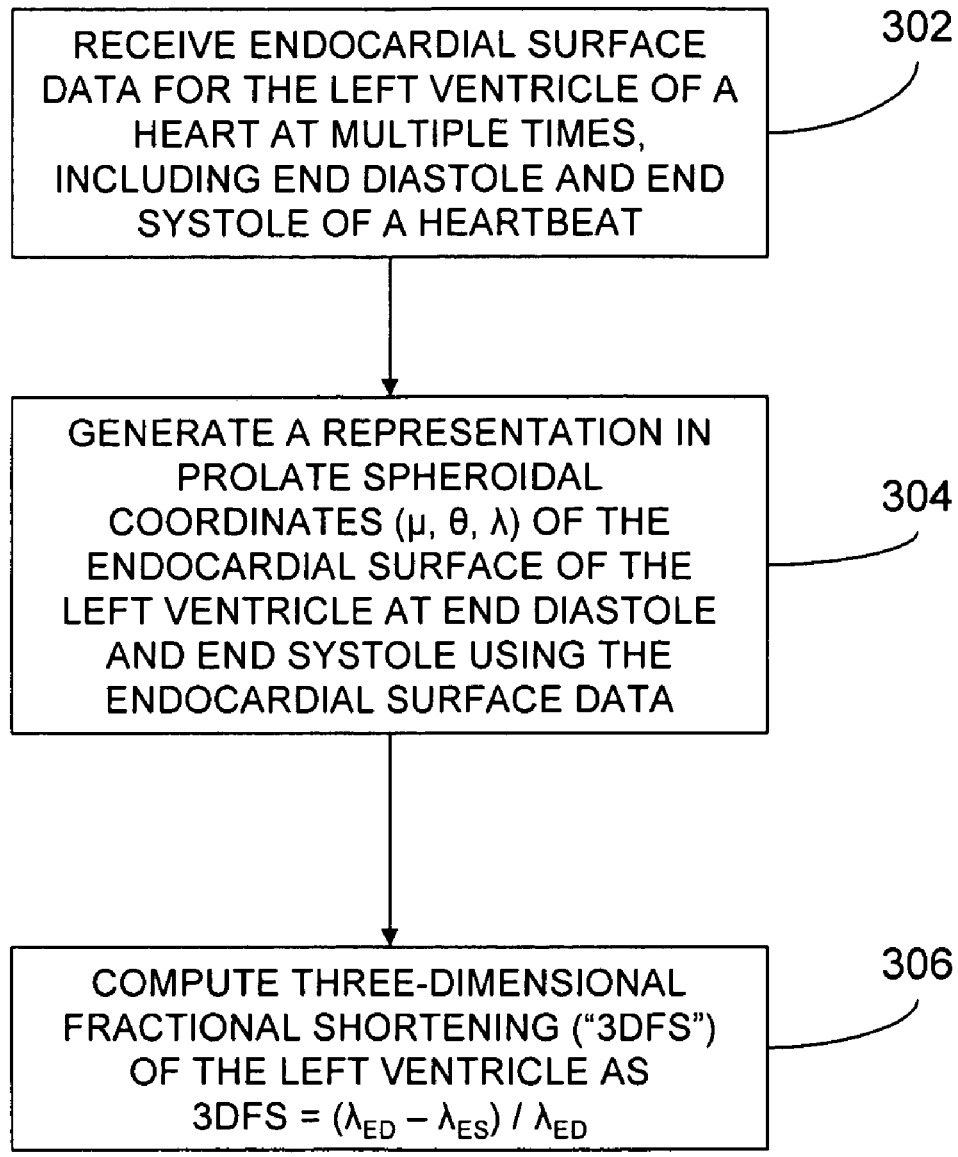
FIG. 3 is an illustrative diagram demonstrating a method for computing three-dimensional fractional shortening of the left ventricle of a heart in accordance with some embodiments of the disclosed subject matter.

FIG. 3 is an illustrative diagram demonstrating a method for computing three-dimensional fractional shortening of the left ventricle in accordance with some embodiments of the disclosed subject matter. Endocardial surface data for the left ventricle of a heart is received that represents the left ventricle at multiple times, including end diastole and end systole of a heartbeat (302 of FIG. 3). A representation in prolate spheroidal coordinates of the endocardial surface of the left ventricle is generated at end diastole and end systole using the endocardial surface data (304 of FIG. 3). The value of coordinate $\lambda$ at end diastole can be represented by $\lambda_{ED}$, and the value of coordinate $\lambda$ at end systole can be represented by $\lambda_{ES}$. Three-dimensional fractional shortening of the left ventricle is computed as follows (306 of FIG. 3):

$$3DFS = (\lambda_{ED} - \lambda_{ES})/\lambda_{ED} \quad (4)$$

As equation (4) indicates, three-dimensional fractional shortening captures the wall motion of the left ventricle from end diastole to end systole, and relates to the contractile function of the heart. Three-dimensional fractional shortening can be used to provide diagnostic information related to, for example, ischemia in the left ventricle or any other suitable diagnostic information. For example, three-dimensional fractional shortening can be used to identify areas of ischemia during stress testing.

Figure 4:
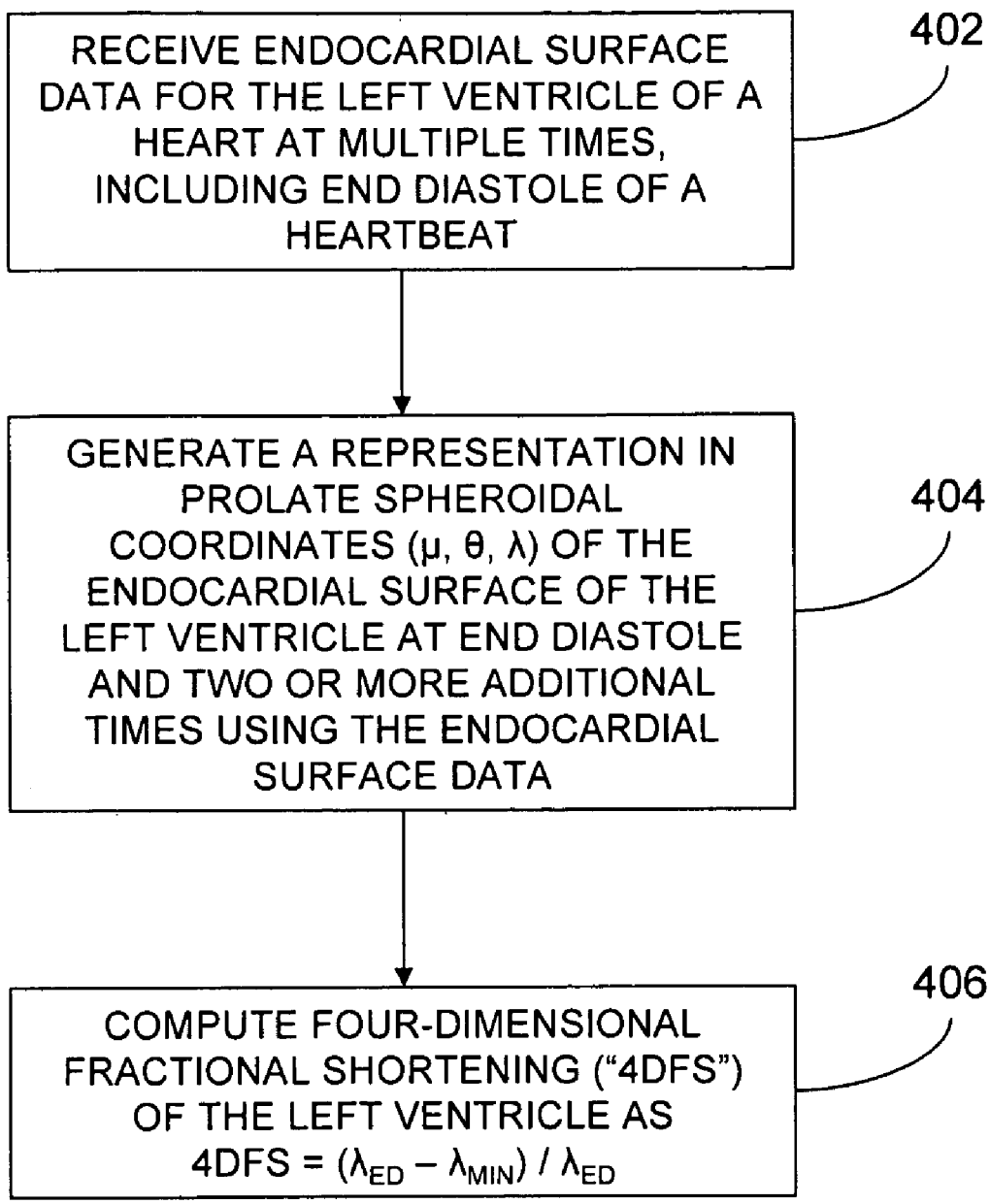
FIG. 4 is an illustrative diagram demonstrating a method for computing four-dimensional fractional shortening of the left ventricle of a heart in accordance with some embodiments of the disclosed subject matter.

FIG. 4 is an illustrative diagram demonstrating a method for computing four-dimensional fractional shortening of the left ventricle in accordance with some embodiments of the disclosed subject matter. Endocardial surface data for the left ventricle of a heart is received that represents the left ventricle at multiple times, including end diastole of a heartbeat (402 of FIG. 4). A representation in prolate spheroidal coordinates of the endocardial surface of the left ventricle is generated at end diastole and two or more additional times using the endocardial surface data (404 of FIG. 4). The value of coordinate $\lambda$ at end diastole is represented by $\lambda_{ED}$, and the minimum value of coordinate $\lambda$ over the heartbeat can be represented by $\lambda_{MIN}$. Four-dimensional fractional shortening of the left ventricle is computed as follows (406 of FIG. 4):

$$4DFS = (\lambda_{ED} - \lambda_{MIN})/\lambda_{ED} \quad (5)$$

As equation (5) indicates, four-dimensional fractional shortening captures the wall motion of the left ventricle from end diastole to the time of maximum contraction over the heartbeat. It should be noted that, while $\lambda_{MIN}$ may occur at the same time as end systole for a heartbeat, such concurrent timing may not be the case. The minimum value of coordinate $\lambda$ over the heartbeat $\lambda_{MIN}$ can be determined by, for example, fitting the prolate spheroidal coordinates to a finite element mesh representing the endocardial surface of the left ventricle. Alternatively, the minimum value of coordinate $\lambda$ over the heartbeat $\lambda_{MIN}$ can be determined as the minimum value of coordinate $\lambda$ generated from the endocardial surface data. Four-dimensional fractional shortening can be used to provide diagnostic information related to, for example, synchrony of contraction in the left ventricle or any other suitable diagnostic information.

The illustrative methods described above in the context of FIGS. 1-4, and the additional methods described herein, can be stored as executable instructions on a computer readable medium as will be understood by one of ordinary skill in the art.

Although the methods set forth herein are described in the context of the left ventricle of a heart, and in particular in the context of receiving endocardial surface data for the left ventricle of a heart, one of ordinary skill in the art will recognize that the methods described herein can be applied in connection with data for other portions of the heart. And, in accordance with the methods described herein, such data can be used to compute a measure that provides diagnostic information related to the portion of the heart for which the data is received. In particular, the methods described herein can be applied to any portion of the heart that undergoes motion over a heartbeat, such that the location of the portion at various times over the heartbeat can be determined and one or more measures can be computed based on that location.

EXAMPLES

The following examples are set forth to aid in the understanding of the disclosed subject matter, and should not be construed to limit in any way the scope of the disclosed subject matter as recited in the claims which follow thereafter.

Example 1

Figure 5:
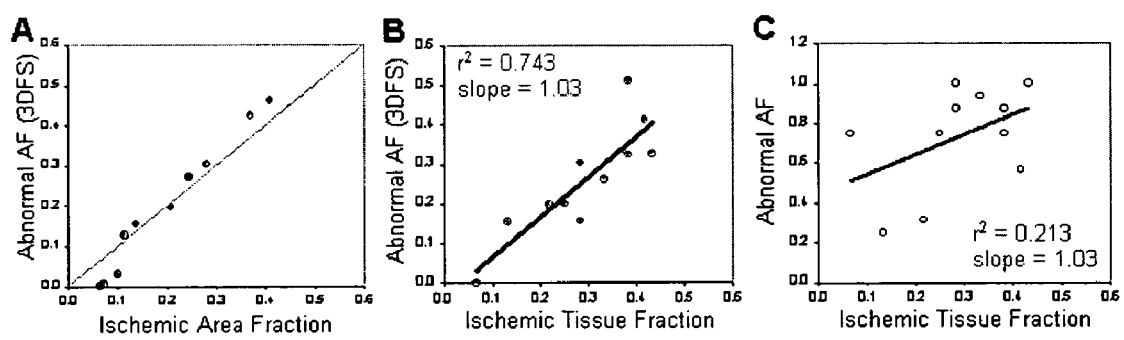
FIGS. 5A-C are plots illustrating a comparison of methods for determining ischemic region size in accordance with some embodiments of the disclosed subject matter.

The size of the wall motion abnormality as assessed by three-dimensional fractional shortening ("3DFS") showed a strong correlation with true ischemic region size predicted by computational models. FIG. 5A illustrates a computational model prediction of the relationship between the fraction of tissue that is acutely ischemic and the fraction of the endocardium ("AF") displaying abnormal wall motion by 3DFS. FIG. 5B illustrates an analysis of eleven brief experimental coronary occlusions in open-chest anesthetized dogs which showed a close relationship between size of wall motion abnormality identified by 3DFS and true ischemic region size by microsphere-based blood flow measurement, as predicted by the model. FIG. 5C illustrates the fraction of the endocardial surface scored as abnormal by an expert cardiologist, which as shown was not significantly correlated with ischemic region size (P=0.15). This result supports that 3DFS in accordance with the methods described herein provides a more accurate measure of ischemic region size than scoring by expert cardiologists, the current state of the art.

This example focuses on a common problem to which four-dimensional cardiac imaging can be applied in accordance with the methods described herein: screening for regions of acute ischemia (i.e., insufficient blood flow) that indicate the presence of coronary artery disease during exercise or pharmacologic stress. The approaches described herein began with knowledge about the biomechanics of acute ischemia and infarction, encoded in finite-element models. This knowledge was then translated from the language of engineering analysis, with its emphasis on stress and strain, to the language of the clinical cardiologist, who describes regional heart function in terms of "wall motion," so that information can be presented to a clinician in a familiar, readily accepted form. Customized measures of wall motion have been developed for detection of acute ischemia in a stepwise fashion, with each new generation of measures requiring more information but providing more accurate and robust diagnosis. In parallel with each new generation of wall motion measures, new image analysis methods have been developed to extract additional information while holding analysis time to a few minutes per patient.

The methods described herein can be used in conjunction with cine-MRI and other four-dimensional imaging methods, and can be applied in areas such as, for example, diagnosis of ischemia and cardiac resynchronization. This example illustrates the application of 3DFS to predicting the size and location of experimentally induced acutely ischemic regions with better accuracy than segment scoring by expert cardiologists. This example illustrates the application of 3DFS during dobutamine stress to detecting and localizing regions of angiographically confirmed coronary artery disease with better accuracy than analysis by expert cardiologists. This example illustrates the application of optical flow tracking from a single manually digitized frame providing endocardial surface data for a full cardiac cycle with similar accuracy to fully manual digitizing. This example illustrates a model-based process to develop new customized 4D wall motion measures to improve quantification of the size, location, and severity of acutely ischemic regions.

A wide variety of cardiac volumetric imaging techniques are available to assess cardiac anatomy, function, and/or perfusion. The choice of imaging modality can depend in part on the question the clinician wants to answer. For example, imaging methods such as SPECT that use radioisotopes to track regional perfusion provide useful information about the distribution of blood flow to different regions of the heart, but provide little information about anatomy. In contrast, intravascular ultrasound, performed by threading an imaging catheter into the coronary arteries that supply blood flow to the heart, can offer a detailed picture of the anatomy of large coronary arteries, helping to identify the precise location and even composition of an atherosclerotic plaque, but does not provide information on pump function of the heart. In many clinical situations, the clinician needs to noninvasively assess function, either the pump function of the entire heart (i.e., global function) or the contributions of specific regions of the heart (i.e., regional function). This example focuses on the imaging of heart function. Options for this purpose include, for example, ultrasound (echocardiography), magnetic resonance imaging ("MRI"), and x-ray ventriculography. Portable, noninvasive, and relatively inexpensive, ultrasound has become the modality of choice among cardiologists. According to the American Society of Echocardiography, roughly fifteen million echocardiograms are performed per year in the United States, nearly one third in offices rather than hospitals.

The essential function of the heart is to pump blood. Therefore, imaging global function of the heart typically involves imaging the blood contained within the ventricles of the heart at different times during the cardiac cycle and inferring how much blood is pumped per beat. In ventriculography, radiopaque dye is injected into the cavity of the ventricle and imaged under x-ray fluoroscopy. With MRI, specific signal-weighting protocols impart different intensities to blood inside the ventricular cavity and the heart muscle surrounding it, allowing the blood to be visualized. In echocardiography, the blood appears as a dark void in the ultrasound image that contrasts with the brighter surrounding muscle. For all these imaging modalities, each image provides a single cross-section through the heart, such that two or more mutually perpendicular images may be needed to get an overall sense of how the blood volume within the ventricular cavity varies over time.

However, clinical decisions are not made based on merely an overall sense of how the blood volume within the ventricular cavity varies over time. A specific quantitative measure, ejection fraction ("EF"), was defined that reflects the relative amount of blood ejected from the left ventricle with each beat: $EF=(EDV-ESV)/EDV$ (where EDV=end-diastolic volume and ESV=end-systolic volume). While there are a number of different methods for estimating ventricular volumes from the images acquired with the modalities set forth above, the critical output from all the analyses is ejection fraction. Ejection fraction has become an important indicator of global cardiac function in clinical cardiology, invaluable in predicting prognosis of patients following myocardial infarction and in assessment and management of patients with heart failure. Thus, while imaging the ventricular cavity was an important step, it was the definition of the quantitative measure ejection fraction that enabled routine evaluation of global cardiac function and the resulting improvements in clinical decision-making and care. In accordance with the methods set forth in this example, the benefits of quantitative measurement are achieved by the imaging of ventricular wall motion.

While some diseases may depress the function of the entire heart fairly uniformly, coronary artery disease usually affects some coronary arteries more than others and thereby some regions of the heart more than others. Therefore, researchers and clinicians have long worked to develop methods for assessing the function of local regions of the heart to supplement the information on global function provided by measurement of cavity volume and ejection fraction described above. Many of the research methods for measuring regional function are invasive and therefore unsuitable for clinical use. For example, researchers have tracked the cyclic shortening and lengthening of a particular segment in the heart wall by implanting pairs of piezoelectric crystals or sonomicrometers that report real-time segment lengths. Implanted radiopaque markers tracked under high-speed biplane x-ray provide similar information, with the added advantage that fully three-dimensional deformations of a small region of heart muscle can be measured. The analysis of deformation or strain in a local region proved to be a useful way to study the mechanical effects of reduced blood flow or ischemia in the laboratory and appeared promising as a method to detect regional ischemia.

With the advent of magnetic resonance tagging, which allows small pieces of heart muscle to be tracked for roughly the duration of a heartbeat without implanting foreign material, three-dimensional strain analysis finally became clinically relevant. Despite continued improvements in tagging methods, a combination of the cost and technical difficulty of these tagging studies, the unfamiliarity of clinicians with the outputs of this analysis (e.g., strains), and the historical preference of most cardiologists for echocardiography over MRI in cardiac imaging have all conspired to limit routine clinical use of MRI tagging studies of regional cardiac mechanics. A series of ultrasound techniques have emerged that offer somewhat less information on the underlying mechanics from an engineering perspective but offer the cardiologist ultrasound-based measures that are more quantitative than standard wall motion scoring. These include tissue-Doppler imaging, strain-rate imaging, and ultrasound elastography. While these techniques still have significant limitations (e.g., angle-dependence, through-plane motion, etc.), their rapid embrace by the cardiology community illustrates the critical need for quantitative noninvasive measures of regional ventricular function as well as the power of applying an appropriate combination of mechanics and clinical expertise to the analysis of regional function.

As physiologists and engineers developed and refined the marker-based approaches described above for use in research on regional ventricular function and dysfunction, cardiologists developed their own methods for clinical evaluation of regional ventricular function from echocardiographic images. As they became familiar with viewing videotaped real-time ultrasound images of cross sections through the heart, cardiologists learned to recognize the normal patterns of motion of the endocardial surface ("wall motion") and deviations in that pattern associated with regional dysfunction due to acute ischemia or a healing myocardial infarct. When its evaluation is carefully standardized, wall motion has proved a useful predictor of coronary artery disease, infarct size, and clinical prognosis.

However, these qualitative assessments are subject to large inter-observer variability, and considerable effort has been expended to develop quantitative measures that index regional function as ejection fraction indexes global function. These attempts have been limited by the same few problems. First, manual tracing of the endocardial border is too time-consuming to be practical for routine clinical use ("segmentation problem"). Second, most two-dimensional analyses require the definition of a centroid and any method for choosing that centroid introduces artifacts ("centroid problem"). Finally, it is difficult to reconstruct a coherent picture of three-dimensional wall motion from a series of two-dimensional views acquired at different times and from different transducer locations ("reconstruction problem"). As described in the remainder of this example, the four-dimensional nature of four-dimensional cardiac imaging methods provides ample data to address these problems in accordance with the methods described herein.

Although cine-MRI has been available for some time and has been used to study endocardial motion, the real excitement among cardiologists about four-dimensional cardiac imaging began when RT3D ultrasound was introduced. It has been shown that the reduction in time required to image the entire left ventricle was an important advantage of RT3D when performing treadmill stress echocardiography to screen for coronary artery disease. In addition, RT3D also rendered tractable each of the classic problems that have limited quantitative wall motion analysis as set forth above. In particular, there is no reconstruction problem when image data are provided as a full three-dimensional volume. In addition, the fact that the entire left ventricle is imaged allows definition of a coordinate system based on landmarks such as the mitral and aortic valves that are far from regions of potential abnormal motion, addressing the centroid problem. Finally, the true four-dimensional nature of the dataset allows more robust approaches to segmentation, since continuity of the endocardial surface in space and time through the image datasets can be used to offset the impact of image noise and local segmentation errors.

Figure 6:
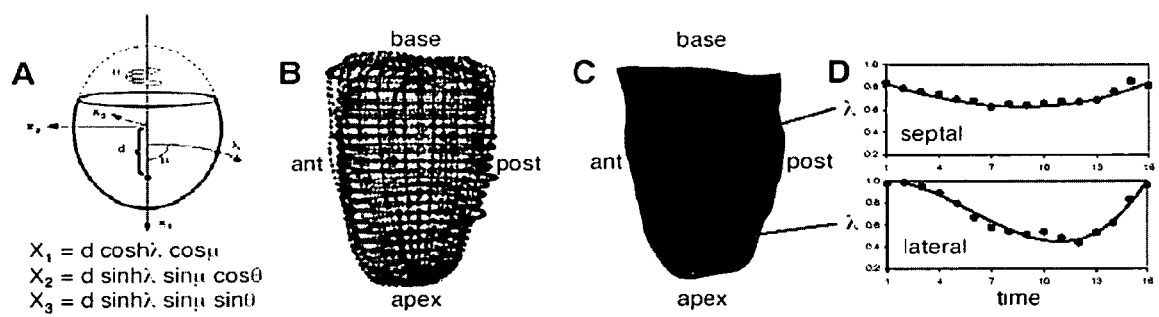
FIGS. 6A-D illustrate the generation of a parameterization of the motion of the left ventricular endocardial surface in space and time in accordance with some embodiments of the disclosed subject matter.

The approach to quantifying wall motion described in this example begins with generating a patient-specific mathematical description or parameterization of the motion of the left ventricular endocardial surface in space and time. The parameterization takes advantage of prolate spheroidal coordinates as illustrated in FIG. 6A, an elliptical coordinate system that advantageously allows the problem of fitting a finite element mesh to left ventricular surface data to be converted from a computationally expensive three-dimensional least-squares problem to a one-dimensional problem. This approach was extended to four dimensions by constructing a finite element mesh from a composition of polynomial spatial and temporal basis functions so that the elliptical coordinate $\lambda$ is defined as a continuous polynomial function of space and time, $\lambda = \lambda(\mu, \theta, t)$. The endocardial surface is digitized using custom software, yielding approximately 5,000 points per time frame as illustrated in FIG. 6B. These points are transformed into prolate spheroidal coordinates and fitted to a finite element mesh with sixty-four spatial elements and a single temporal element constructed from polynomial basis functions. The prolate spheroidal coordinate system is defined by the center of the mitral valve ring, the left ventricular apex, and the mid-septum, removing translation and rotation without requiring the definition of a centroid.

The data from a full cardiac cycle (e.g., 15-20 frames) are then fitted to the four-dimensional finite element mesh, yielding a concise description of the endocardial surface in both space and time, as illustrated in connection with FIGS. 6C and D, respectively. In FIG. 6D, the motion of two different nodes on the finite-element mesh over the full cardiac cycle is illustrated, in which the solid line shows four-dimensional fit and the individual points show three-dimensional fits to data from individual time frames. The endocardium is treated as a finite element mesh evolving in time. Parameter values, namely $\lambda$ and spatial derivatives of $\lambda$, defined at spatiotemporal nodes allow for a compact representation of the complex shape of the endocardial surface throughout the cardiac cycle. To interpolate $\lambda$ at other locations or times, basis functions are evaluated to determine the relative contribution of the nodal parameters. Spatially, cubic Hermite basis functions are used to ensure $C^1$ continuity, preventing sharp cusps between elements. The temporal domain is represented by a single Lagrange element. In this dimension, cubic Lagrange basis functions adequately describe the behavior of $\lambda$ throughout the cardiac cycle (FIG. 6D). For spatial coordinates, $\xi_1$ and $\xi_2$, and temporal coordinate, $\xi_t$, the governing equation is expressed as:

$$\lambda(\xi_1,\xi_2,\xi_t) = \Lambda_0(\xi_1,\xi_2)L_0(\xi_t) + \Lambda_{1/3}(\xi_1,\xi_2)L_{1/3}(\xi_t) + \Lambda_{2/3}(\xi_1,\xi_2)L_{2/3}(\xi_t) + \Lambda_1(\xi_1,\xi_2)L_1(\xi_t) \qquad (6)$$

where $\Lambda_x$ represents the finite element mesh at the temporal node corresponding to $\xi_t = x$ and is computed according to Hashima et al. "Nonhomogeneous analysis of epicardial strain distributions during acute myocardial ischemia in the dog," J Biomech, 26:19-35, 1993. The fitting process calculates the set of nodal parameters that minimizes the difference between the spatiotemporal data and the resulting endocardial surface in the least squares sense. Taking advantage of the fact that the endocardial surface is fairly smooth in both space and time and the use of higher-order basis functions, the fitted surface at a single time can be represented by just 288 nodal parameters and the full cardiac cycle by just four times that number, a 200-fold data reduction from the original digitized coordinate data.

Figure 7:
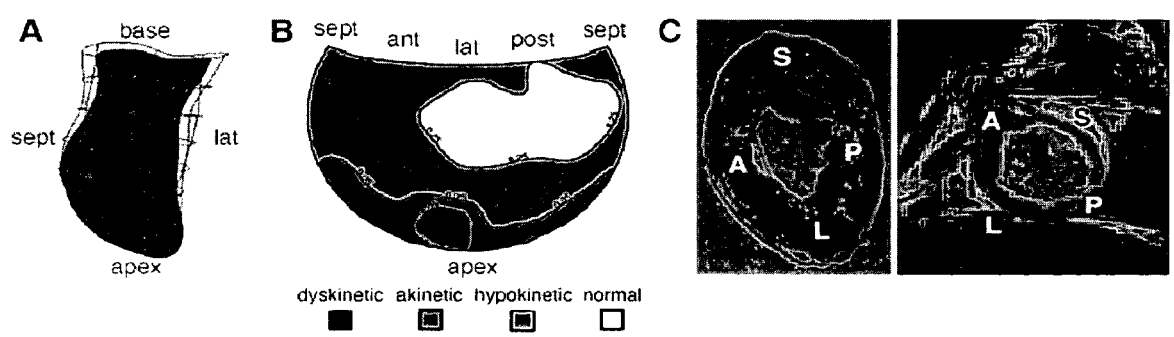
FIGS. 7A-C illustrate the calculation and mapping of three-dimensional fractional shortening for a sheep with anteroseptal infarction in accordance with some embodiments of the disclosed subject matter.

This parameterization represents a complete, concise description of the motion of the endocardial surface from which any desired measure of wall motion can be computed. For example, the change in the coordinate $\lambda$ of any point on the surface from end diastole to end systole can be used as a direct measure of regional wall motion. The partial derivatives $\partial\lambda/\partial\mu$ and $\partial\lambda/\partial\theta$ provide information on curvature and the derivative $\partial\lambda/\partial t$ provides information on the rate of motion for any point on the surface at a given time. It should be noted that while the process of identifying the endocardial surface (e.g., segmentation) and some of the coordinate transformations depend on the modality used to image the heart, the parameterization process and all subsequent wall motion analysis are independent of the imaging method, and are therefore equally valid for real-time three-dimensional ultrasound (RT3D), MRI, and any other current or future four-dimensional imaging methods. For example, FIGS. 7A-7C illustrate calculation and mapping of 3DFS based on MRI images of a sheep with an anteroseptal infarction. In FIG. 7A, the wire frame shows fit at end diastole, and the solid surface shows fit at end systole. In FIG. 7B, 3DFS has been computed as the fractional change in the coordinate $\lambda$ and plotted as a 2D contour map that preserves relative surface areas. This type of map is also referred to herein as an "area preserving map." The map in FIG. 7B indicates depressed global function, akinesis in the septum, and dyskinesis at the apex. In FIG. 7C, gross pathology for the heart, shown next to a short-axis MRI slice, confirmed that the infarct occupied the lower septum (S) and apex (A).

Once a parametric representation of endocardial motion has been obtained, an unlimited number of different measures of wall motion can be computed from that parameterization in accordance with the methods described herein. The goal was to design measures that provide clinically useful information. One such measure is three-dimensional fractional shortening, described above. By comparing the end-diastolic and end-systolic values of the prolate spheroidal coordinate $\lambda$, a fractional shortening is calculated for every point on the endocardial surface as $3DFS=(\lambda_{ED}-\lambda_{ES})/\lambda_{ED}$. 3DFS can be displayed on a two-dimensional contour map (e.g., FIG. 7B).

One approach to classifying the motion of regions of the endocardial surface based on 3DFS values is based on established practice guidelines for two-dimensional segmental wall motion analysis. In this approach, regions of the endocardial surface are classified into the clinically familiar categories normal (3DFS>0.25), hypokinetic (0.05<3DFS≦25), akinetic (−0.05<3DFS≦0.05), or dyskinetic (3DFS≦−0.05) and the 3DFS map can be color-coded accordingly (e.g., FIGS. 7B, 8B). However, in some situations baseline function may already be depressed. This is true in experiments on open-chest anesthetized dogs, where global cardiac function is known to be depressed even at baseline. This problem of depressed baseline function is also clinically relevant, since patients with heart failure or prior infarction may also have depressed regional function at baseline. In analyzing these studies, abnormal wall motion is defined herein based on the change in 3DFS from baseline rather than on its absolute value (e.g., FIG. 9A).

Figure 8:
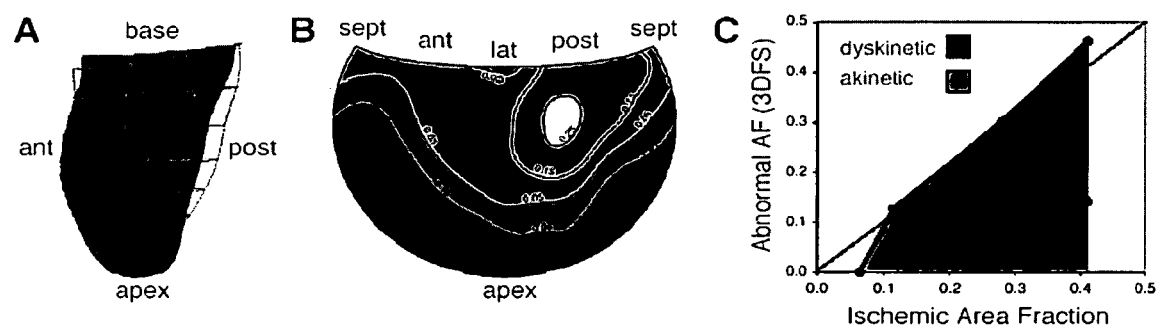
FIGS. 8A-C illustrate the simulation and mapping of a largely acute ischemic region in an anterior wall and apex of the left ventricular endocardial surface in accordance with some embodiments of the disclosed subject matter.

In connection with developing the custom wall motion measure described herein, in silico screening was performed. A sophisticated finite element model of the regionally ischemic left ventricle was adapted to simulate acutely ischemic regions of varying sizes and the size of the endocardial region displaying abnormal values of 3DFS was compared to the size of the simulated ischemic region. It was found that the fraction of the endocardial surface with 3DFS<0.05 (akinetic+dyskinetic regions) was linearly related to the fraction of the endocardial surface that was ischemic over a wide range, suggesting that 3DFS may have excellent predictive value for determining the size of acutely ischemic regions (FIGS. 8A-8C). FIG. 8A illustrates the left ventricle endocardium at end diastole (wire mesh) and end systole (solid surface) during simulation of a large acutely ischemic region (darker portion) in the anterior wall and apex. FIG. 8B is a map of 3DFS showing large regions of dyskinesis (black) and akinesis (dark gray). Hypokinesis (light gray) over much of remaining surface is due to the fact that the model is based on data from open-chest anesthetized animals. FIG. 8C is a plot of the fraction of the endocardial surface displaying akinesis and dyskinesis compared to the fraction occupied by the simulated ischemic region. The linear relationship with a slope near 1.0 suggests that the area displaying abnormal 3DFS provides a good estimate of ischemic region size above a critical size of 10%. It was also found that even in the best case of model data without image noise or segmentation error, the relationship between abnormal wall motion and ischemic region size broke down below an ischemic region size of 10%, with ischemic regions of 7% of the left ventricle inducing no detectable wall motion abnormality. This observation reflects the fact that small ischemic regions are coupled on all sides to normal myocardium, and below some critical size simply get carried along by the motion of the adjacent myocardium, inducing no detectable wall motion abnormality. The ability to identify and compare such fundamental physical limits to different detection strategies is an important advantage of the model-based approach.

As a preliminary test of the ability of 3DFS to identify the size and location of an experimentally induced ischemic region, the left ventricles of three open-chest isoflurane-anesthetized dogs were imaged using RT3D ultrasound (Philips iE33) during brief (<2 minutes) distal and proximal occlusions of the left anterior descending (LAD) and left circumflex (LCx) coronary arteries. Colored microspheres were injected during each occlusion to map the regions of the left ventricle deprived of at least 50% of control blood flow. The size and location of the ischemic region as identified by blood flow measurements were compared to the predicted size and location based on 3DFS computed from fitted endocardial surfaces. As will be described in connection with FIGS. 9A-F, 3DFS-predicted ischemic region size corresponded closely to true ischemic region size across a total of eleven occlusions performed in three dogs, with an $r^2$ value of 0.74 and a slope of 1.03 (P<0.001). This result was nearly identical to the computer model predictions (FIGS. 5A-C, 8C). By contrast, the fraction of the endocardial surface scored as abnormal by an expert cardiologist was not significantly correlated with true ischemic region size (P=0.15).

Figure 9:
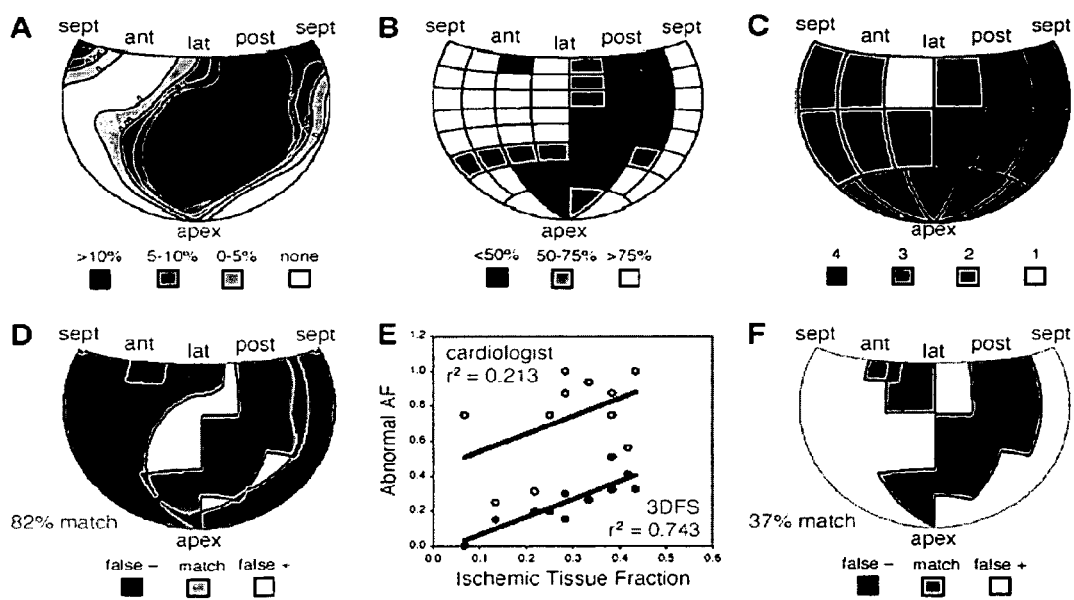
FIGS. 9A-F illustrate a comparison of predictions for locations of ischemic regions of the left ventricle in accordance with some embodiments of the disclosed subject matter.

FIG. 9A illustrates a map of changes in 3DFS from baseline during occlusion of the distal LCx coronary artery in a typical dog. As shown, 3DFS dropped more than 10% from baseline in the regions shaded in black. FIG. 9B illustrates a map of regional blood flow distribution during the same occlusion. In FIG. 9B, regions with <50% of control blood flow are shaded in black. FIG. 9C illustrates the scoring of an expert cardiologist, indicating that most segments were scored either hypokinetic (2) or akinetic (3) during this occlusion. FIG. 9D illustrates the difference between maps of abnormal wall motion by 3DFS and ischemic region by blood flow. In FIG. 9D, regions of agreement are shaded in gray. FIG. 9E provides a plot indicating that 3DFS-predicted ischemic region size correlated well with true ischemic region size across a total of eleven occlusions in three dogs, while size of regions with abnormal segment scores did not correlate as well. FIG. 9F illustrates the difference between maps of abnormal wall motion by segment scoring and ischemic region by blood flow.

3DFS (FIG. 9A) and expert scoring (FIG. 9C) were each used to divide the endocardial surface into normal and abnormal (>10% reduction in 3DFS or wall motion score>1) regions. These maps of predicted ischemic region location were subtracted from the blood flow map (FIG. 9B) to determine which portions of the surface were classified correctly ("match"), as well as which portions were erroneously classified as ischemic ("false positive") or normal ("false negative"). In the example shown, 3DFS correctly classified 82% of the endocardial surface (FIG. 9D), while cardiologist scoring correctly classified just 37% (FIG. 9F). On average for the eleven occlusions analyzed, 3DFS correctly classified 72±11% of the endocardial surface, segment scoring 52±14% (P=0.01). Overall, this data strongly supported that reduced 3DFS predicts the size and location of experimentally induced ischemic regions with better accuracy than segment scoring by expert cardiologists.

Figure 10:
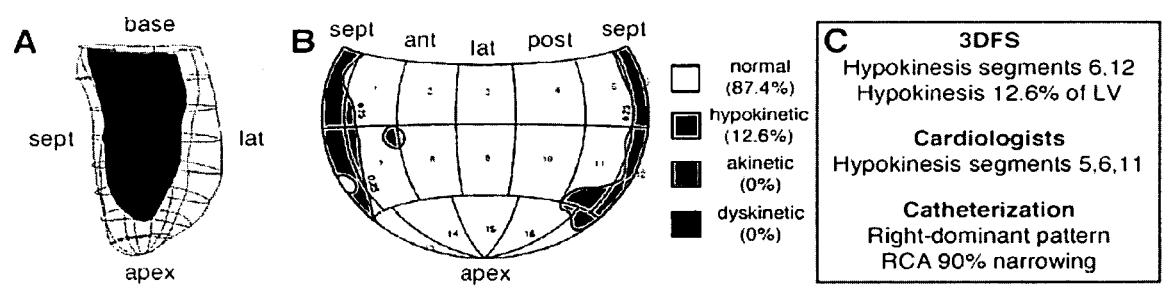
FIGS. 10A-C illustrate a comparison of three-dimensional fractional shortening to expert scoring and angiography in accordance with some embodiments of the disclosed subject matter.

A pilot study was conducted in fourteen patients to evaluate the utility of contrast agents and used data from the same study to compare semi-quantitative wall motion scores from two expert cardiologists to 3DFS-based classification of wall motion in patients undergoing clinically indicated dobutamine stress echocardiography. Patients were imaged with the Philips SONOS 7500 RT3D ultrasound system at rest and during peak dobutamine infusion with and without contrast. Contrast significantly increased the number of adequately visualized segments both at rest and during dobutamine infusion, as expected based on prior results for two-dimensional echo. Two expert cardiologists reviewed fourteen contrast datasets (rest and stress from seven patients) and assigned a semi-quantitative score to each of the sixteen standard segments in each dataset as follows: 1 for normal wall motion, 1.5 for mild, 2 for moderate, 2.5 for severe hypokinesis, 3 for akinesis, and 4 for dyskinesis. The LV endocardial border was manually traced, a three-dimensional surface fit to the digitized points, and regional three-dimensional fractional shortening calculated and interpolated from continuous maps at the center of each of the sixteen standard LV segments. FIGS. 10A-C illustrate a comparison of 3DFS to expert scoring and angiography. In FIG. 10A, the wire frame shows the surface fit at end diastole, and the solid surface shows the surface fit at end systole during dobutamine stress. In FIG. 10B, 3DFS indicated hypokinesis in the septum and inferior wall, covering 12.6% of the LV endocardium and suggesting clinically significant stenosis in the right coronary artery (RCA). In FIG. 10C, qualitative scoring by expert cardiologists agreed and angiography confirmed that clinically significant stenosis was present in the RCA. In particular, a 3DFS-based wall motion score was generated for comparison to the clinical scores by defining >25% 3DFS as normal, 20%-25% as mild, 10%-20% as moderate, 5%-10% as severe hypokinesis, 0%-5% as akinetic, and negative values as dyskinetic. 96% of the segments were visible to the cardiologists, who scored 80% of the visible segments as normal and 20% hypokinetic. By quantitative analysis, 83% of the visible segments were normal, 16% hypokinetic, and 1% akinetic. Cardiologist and quantitative scores agreed within 0.5 in 83% of all segments scored.

Figure 11:
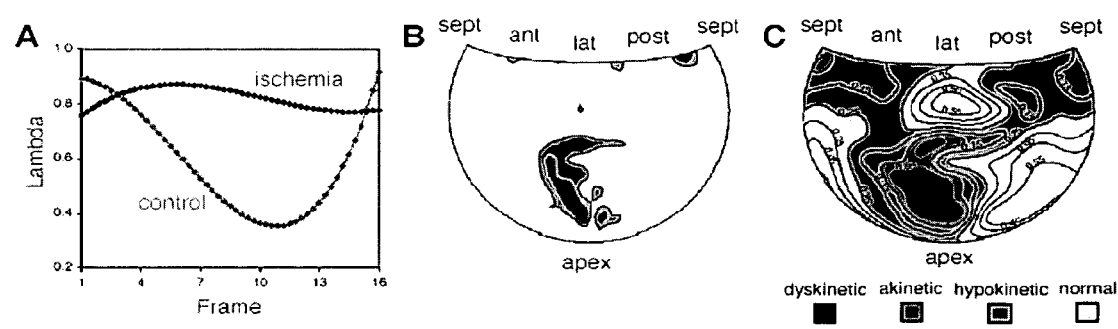
FIGS. 11A-C illustrate the local rate of inward/outward motion (d$\lambda$/dt) for canine pilot data in accordance with some embodiments of the disclosed subject matter.
Figure 13:
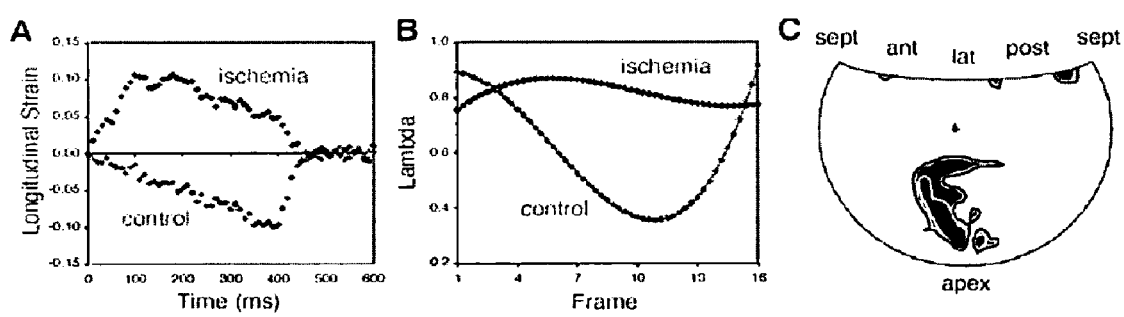
FIGS. 13A-C illustrate the detection and quantification of regional ischemia using four-dimensional analysis in accordance with some embodiments of the disclosed subject matter.

During normal contraction, local shortening and thickening of the myocardium proceed gradually throughout systole, reaching their peak at or near end-systole (also see FIGS. 13A-C). By contrast, during acute ischemia the ischemic myocardium converts from an active to a passive material and simply stretches or recoils in proportion to the local wall stress. Since wall stress rises very rapidly during isovolumic contraction (IVC) and reaches its maximum at end IVC, stretching of the ischemic region follows the same pattern. Based on this finding, acute ischemia may be detected based on four-dimensional wall motion analysis by looking for regions that move outward rather than inward during isovolumic contraction. In the canine pilot data, it was found that the local rate of inward/outward motion ($d\lambda/dt$) is a more specific indicator of regional ischemia than 3DFS. FIGS. 11A-C provide an example of the added benefit of fully four-dimensional analysis for detecting regional ischemia during temporary occlusion of the left circumflex coronary in a dog. In FIG. 11A, control wall motion is gradually inward throughout systole, while the ischemic region shows initial outward motion during isovolumic systole. FIG. 11B illustrates the mapping of the rate of outward wall motion, which clearly identifies the ischemic region (shaded in gray). In FIG. 11C, 3DFS identified the same ischemic region but also picked up reduced motion in the basal septum that was not due to ischemia. These results suggested that $d\lambda/dt$ (FIG. 11B) may be a more specific indicator of acute ischemia than 3DFS (FIG. 11C).

While the amount of motion observed in normal regions varied widely, all of these regions moved gradually inward throughout systole. By contrast, dyskinetic acutely ischemic regions moved rapidly outward during isovolumic contraction, then inward later in systole. By making this type of fully four-dimensional analysis accessible and practical, the methods described herein can allow clinicians to take full advantage of the four-dimensional nature of the underlying cardiac image data.

In order to produce clinically useful measures based on fully four-dimensional analysis, the relevant data is extracted from four-dimensional images. In the case of cardiac MRI, automated segmentation routines can be used. However, segmentation of RT3D ultrasound presents special challenges. Although image segmentation work often has as its ultimate goal the fully automated segmentation of medical images, this goal remains elusive for RT3D ultrasound images. Currently, the best available segmentation routines make frequent local errors, overestimating the local distance from the center of the cavity about as often as the distance is underestimated.

Figure 12:
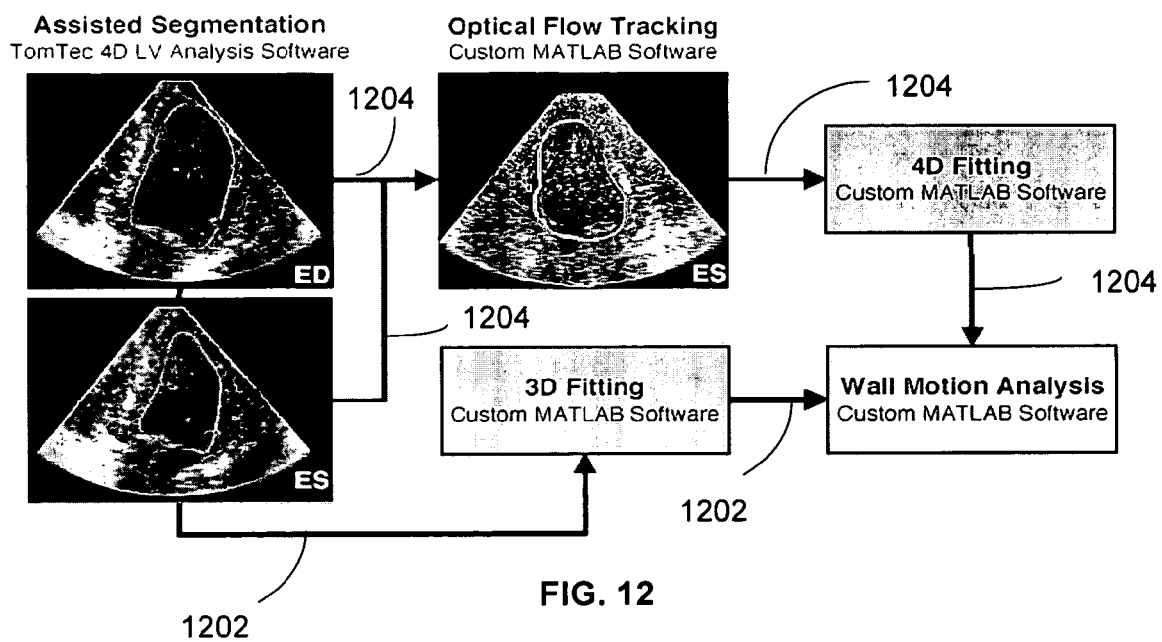
FIG. 12 is an illustrative diagram demonstrating the flow of information in a four-dimensional analysis framework in accordance with some embodiments of the disclosed subject matter.

As a result, current commercial software packages for RT3D images (e.g., 4D LV-Analysis by TomTec and QLAB from Philips) utilize assisted segmentation, displaying automatically generated initial contours and allowing the user to edit them to obtain a satisfactory representation of the endocardial surface. With QLAB, assisted segmentation of RT3D data from two time frames (end diastole and end systole) for a high-quality dataset required just three minutes for an experienced user. TomTec's 4D LV-Analysis required twelve minutes but had the advantage over QLAB that it readily exported data points from the resulting segmentation. 3DFS as described herein can be computed from the resulting assisted-segmentation data in just a few more seconds, providing valuable new information for a modest overall time investment by the user. In connection with fully four-dimensional analysis, algorithms have been developed based on the concept of optical flow to track points segmented in end-diastolic and end-systolic time frames through intermediate time frames and construct a full segmentation of all time frames without additional input from the user. FIG. 12, for example, illustrates the flow of information in a four-dimensional analysis framework. Assisted manual segmentation of end-diastolic (ED) and end-systolic (ES) images requires just minutes with commercial software (left panels). For three-dimensional analysis, the ED and ES contours are exported directly to custom software (e.g., custom software using MATLAB) for fitting and wall motion analysis (arrows 1202), which can take only a few additional minutes. To obtain fully four-dimensional endocardial information with minimal additional user effort, optical flow can be used to track the endocardial surface between the manually identified ED and ES locations. Surface data can then be passed to software routines (e.g., software routines using MATLAB) for four-dimensional fitting and wall motion analysis (arrows 1204). The images shown in FIG. 12 are from a dog imaged as part of the pilot studies described above.

The wall motion measure three-dimensional fractional shortening described herein has performed extremely well in a range of tests and can have an impact on clinical research. One possible clinical application for this measure is stress echocardiography, where myocardial oxygen demand is increased by exercise or pharmacologic stress, causing regions with significant coronary disease to become temporarily ischemic and to move abnormally.

As described above, 3DFS is a generalization to three dimensions of the "fractional shortening" measure that can be calculated from short-axis echocardiograms (FIGS. 7A-C). The following data support the value of 3DFS for detecting and quantifying wall motion abnormalities arising from acute regional ischemia. First, in model experiments 3DFS provided an accurate measure of ischemic region size during simulated total coronary artery occlusion. The fraction of the endocardial surface displaying 3DFS<0.05 was linearly related to the fraction of the endocardial surface on which simulated ischemia was imposed, above a threshold ischemic region size of 10%. Second, in canine experiments, ischemic region size predicted by a >10% drop in local 3DFS was strongly correlated with ischemic region size determined independently by regional blood flow measurements. Third, in a clinical pilot study of patients undergoing dobutamine stress echocardiography, 83% of segment scores based on 3DFS agreed with consensus scoring by two expert cardiologists.

A challenge in validating a quantitative measure of wall motion is that there is no wall motion gold standard. Studies comparing visual wall motion scoring during stress echocardiography to presence of clinically significant coronary artery narrowing on cardiac catheterization typically report values of about 80% for sensitivity, specificity, and inter-observer agreement of wall motion scoring, similar to the 83% agreement between 3DFS and wall motion scoring in the clinical pilot study described herein. Two approaches to obtain a more rigorous validation of 3DFS are: (1) validate 3DFS using animal experiments that provide quantitative measures of ischemic region size, location, and severity but translate less directly to the clinical setting; or (2) validate 3DFS against findings on cardiac catheterization, which provides a semi-quantitative and spatially coarse but independent measure of the presence and severity of coronary artery disease and is the accepted gold standard in cardiology literature.

Embolization with 100-μm polymer beads can be used to gradually reduce blood flow to selected target regions in isoflurane-anesthetized dogs while RT3D images are acquired. Multiple embolizations can provide data at different degrees of blood flow reduction in each dog, while a range of ischemic region sizes can be achieved over the course of the study by varying the location of the embolization catheter within the coronary artery tree in different dogs. Colored microspheres can be used to quantitatively map the location, spatial extent, and degree of blood flow reduction in the induced ischemic region, providing quantitative validation of 3DFS-based estimates of ischemic region size and location. In the first half of the animals, the chest can be opened and sonomicrometers implanted to obtain an independent measure of the degree of impairment of regional mechanics achieved at various degrees of blood flow reduction. Subsequently, experiments can be conducted in the closed-chest state to better simulate the clinical setting. The accuracy of the 3DFS-based estimates described herein can be compared to the accuracy of blinded wall motion scoring by expert cardiologists, using the standard sixteen-segment model and methods recommended by the American Society of Echocardiography.

Surgical procedures are outlined in more detail below. Briefly, twenty dogs can be anesthetized and ventilated. In half the animals, a thoracotomy can be performed for placement of sonomicrometers. In the other half, the chest can remain closed and coronary catheters can be placed under fluoroscopic guidance. All animals can be instrumented with catheters for left ventricular pressure measurement, colored microsphere injection (left atrium), reference blood sampling (descending aorta), and polymer-bead embolization. Regional ischemia of increasing severity can be induced by embolization with four sequential boluses of 50,000 100-μm polymer beads injected directly into the selected coronary artery. Real-time three-dimensional echocardiographic data can be obtained immediately prior to embolization and at five minutes after each bolus. Simultaneous with the imaging sequences for each occlusion, colored microspheres can be injected into the implanted left atrial catheter and blood sampled from the aortic catheter to allow measurement of blood flow to quantify the ischemic region size, spatial extent, and severity.

Endocardial surfaces can be identified at end diastole and end systole by assisted manual tracing in, for example, TomTec 4D LV-Analysis CRT Software 2.0 and the endocardial data exported. These data can be fitted to the four-dimensional finite element mesh described above, defined in terms of λ and spatial derivatives of λ at spatiotemporal nodes using cubic Hermite basis functions in the spatial domain and cubic Lagrange basis functions in the temporal domain. For spatial coordinates, $\xi_1$ and $\xi_2$, and temporal coordinate, $\xi_t$, the governing equation is expressed as:

$$\lambda(\xi_1,\xi_2,\xi_t)=\Lambda_0(\xi_1,\xi_2)L_0(\xi_t)+\Lambda_{1/3}(\xi_1,\xi_2)L_{1/3}(\xi_t)+\Lambda_{2/3}(\xi_1,\xi_2)L_{2/3}(\xi_t)+\Lambda_1(\xi_1,\xi_2)L_1(\xi_t) \qquad (6)$$

where $\Lambda_x$ represents the finite element mesh at the temporal node corresponding to $\xi_t$=x and is computed according to Hashima et al. The fitting process calculates the set of nodal parameters that minimizes the difference between the spatiotemporal data and the resulting endocardial surface in the least squares sense. By comparing the end-diastolic and end-systolic values of the prolate spheroidal coordinate λ, three-dimensional fractional shortening can be calculated for every point on the endocardial surface as 3DFS=$(\lambda_{ED}-\lambda_{ES})/\lambda_{ED}$ and this measure can be displayed on a two-dimensional contour map. Alternatively, this measure can be displayed on a circumferential polar plot of the left ventricle. Since baseline function is depressed in experiments on open-chest anesthetized dogs, abnormal wall motion can be defined as a 10% drop in 3DFS from non-ischemic baseline rather than on its absolute value.

Wall motion scoring can be conducted by expert cardiologists blinded to the experimental condition, using the standard sixteen-segment model and methods recommended by the American Society of Echocardiography. Since baseline function is depressed in experiments on open-chest anesthetized dogs, in analyzing these studies, two different methods of defining abnormal wall motion based on segment scores can be considered. In the first method, any segment scored as abnormal by the blinded expert cardiologists can be considered abnormal. In the second method, those segments that scored worse during ischemia than at non-ischemic baseline can be considered abnormal.

Colored microspheres can be rapidly infused into the left atrium and reference blood samples withdrawn at 7 ml/min for two minutes beginning just prior to microsphere injection at five times: in the initial control state and five minutes after each of the four embolizations. Following the experiment, the heart can be divided into sixty-four transmural blocks (approximately 1 g each) corresponding to the sixty-four spatial elements in the finite element mesh used for wall motion analysis. Blood flow can be calculated from the CMS data for each block according to standard techniques. Blood flow can be mapped using the same mapping techniques for wall motion. Initially, a cutoff of 50% of control blood flow can be used to separate ischemic from non-ischemic regions (e.g., FIGS. 9A-F).

Five expert cardiologists can score each image dataset (80 post-embolization and 20 pre-embolization baseline images). Each cardiologist can also manually segment each image dataset, and the resulting data can be fitted and analyzed as described above. The regressions of abnormal area fraction determined by 3DFS or by segment scoring can be compared against ischemic region size based on measured blood flow (FIGS. 9A-F). For each individual cardiologist, the significance of a difference between these correlation coefficients can be determined by transforming them using the Fisher transformation $Z(r)$ and computing the test statistic $z=(Z_1-Z_2)/\sigma_{Z1-Z2}$. For the example shown in FIGS. 9A-F, the z statistic was 1.606 (P=0.123), not quite significant at n=11. In addition to analyzing the degree of correlation, the RMS error in predicting ischemic region size can be computed for each cardiologists' segment scores and for 3DFS analysis based on each cardiologists' segmentation.

Five expert cardiologists can score each image dataset (80 post-embolization and 20 pre-embolization baseline images). Each cardiologist can also manually segment each image dataset, and the resulting data can be fitted and analyzed as described above. The percentage of the endocardial surface correctly classified as ischemic or non-ischemic based on 3DFS or on segment scoring can be compared (e.g., FIGS. 9A-F). For each individual cardiologist, the percentage of the surface correctly classified by segment scoring and by 3DFS analysis for all 80 embolizations can be compared by paired t test.

The most important difference between the model and pilot experiments used to predict the anticipated results and the studies conducted is the severity of the induced ischemia. While the model simulates a fully transmural ischemic region, even complete coronary occlusion rarely produces fully transmural ischemia, and stress in a patient with limited coronary flow reserve produces a much smaller relative deficit in regional blood flow than complete coronary occlusion. The proposed strategy of sequential embolization is designed to produce subtler blood flow reductions than total coronary occlusion, allowing for the exploration of wall motion abnormalities more like those expected in a clinical setting. The relationship between ischemic region size and 3DFS-identified wall motion abnormality described above in connection with the computational modeling and observed in the pilot study may depend on the severity of ischemia. In that case, correlations that group data from experiments with varying degrees of ischemia may be weaker than anticipated. Because stress tests are terminated if there is evidence of significant ischemia (e.g., chest pain, EKG changes, etc.), the range of ischemia severity actually experienced by patients during dobutamine stress tests may be fairly narrow. Four-dimensional wall motion measures described herein may provide better quantification of the severity of ischemia.

Regression analysis usually focuses on comparing slopes or intercepts, particularly when comparing two different methods of analysis. However, when evaluating predictions of ischemic region size, the degree of variation about the regression line can be compared, as reflected in the regression coefficient and RMS error. This is because, to accurately predict ischemic region size, the specific values of the slopes and intercepts are not critical. Hence, of interest is the predictive value of the regression rather than the specific values of its coefficients.

In some respects, the comparison to segment scoring shown in FIGS. 9A-F is unfair to the scoring cardiologists. Although the regression was not significant at the sample size shown, the slope of the line was near one. The striking difference compared to 3DFS was an intercept near 40% of the LV surface. This finding is reasonable—it reflects significant abnormal motion even at baseline, which is true for an open-chest anesthetized dog due to the depression of baseline function. In normal clinical practice, the cardiologist compensates for situations such as depressed baseline function by knowing the patient's history and taking it into account. In the blinded analysis, this is not possible. On the other hand, this demonstrates an advantage of the 3DFS methodology described herein. In particular, much of the problem with stress echocardiography is inter-observer variability that arises from different cardiologists integrating information from the history and the images differently. The methods described herein can allow cardiologists to conduct analyses that have better inter-operator agreement and are robust to problems such as altered baseline function.

The results of the wall motion analysis can depend in part on the quality of the acquired images, so variability in image quality is a potential source of error. However, one of the major advantages of RT3D ultrasound for stress echocardiography is that acquisition from a single transducer position reduces dependence on sonographer skill compared to two-dimensional echo. In open-chest animals, the major challenge is that placing the transducer directly on the apex typically excludes some of the apical endocardium from the field of view. In this example, ultrasound gel spacers can be placed between the transducer and the heart. Closed-chest echocardiography in some species (e.g., sheep) has been reported to require laparotomy for sub-diaphragmatic transducer positioning. While this approach may be employed if needed, in dogs it has been found that satisfactory images can be obtained without surgery.

3DFS-based analysis of rest and stress contrast-enhanced RT3D images obtained during clinically indicated dobutamine stress echocardiography can also be used to identify regions in which wall motion becomes abnormal during stress. The 3DFS-based localization of the abnormality can be used to predict whether significant coronary artery disease is present in each of the three major coronary arteries, and this prediction can be tested against the independently determined presence or absence of clinically significant (>50%) stenosis on follow-up angiography (see FIGS. 10A-C for an example from the pilot study). This is the accepted approach in the cardiology literature to determining sensitivity and specificity of qualitative wall motion scoring, as reflected in the thirty-seven studies reviewed in ACC/AHA/ASE 2003 Guideline Update for the Clinical Application of Echocardiography, Table 5: Diagnostic Accuracy of Dobutamine Stress Echocardiography in Detecting Angiographically Proved CAD. For comparison of 3DFS-based methods to current clinical practice, five expert cardiologists can perform blinded wall motion scoring on each RT3D stress study. Specifically, it can be tested whether the sensitivity, specificity, and diagnostic accuracy of 3DFS-based diagnosis of clinically significant coronary stenosis on follow-up angiography are significantly different from the sensitivity, specificity, and diagnostic accuracy of blinded wall motion scoring by expert cardiologists.

Patients referred for clinically indicated dobutamine stress echocardiography due to moderate to high clinical suspicion of CAD or the primary physician's decision to obtain additional diagnostic information following a positive thallium stress test can undergo a standard dobutamine infusion protocol as recommended by the American College of Cardiology. Dobutamine can be infused at progressively higher concentrations (5, 10, 20, 30, 40 micrograms/kg/min over a period of three minutes at each stage) to increase heart rate and inotropic state. The endpoint for the stress test can be attainment of a target heart rate (85% of the predicted maximum heart rate for age), evidence of significant ischemia with associated symptoms and EKG changes (2 mm horizontal or down-sloping ST segment depression), or concerning arrhythmias or other safety concerns by the supervising cardiologist. If the target heart rate is not reached, atropine (0.5 to 1 mg) can be used as per standard protocol to reach the target heart rate. Full volume apical and three-dimensional short axis images can be obtained both at rest and at peak dobutamine infusion with, for example, the Philips iE33, using the FDA-approved contrast agent Definity.

The decision regarding whether to proceed to angiography can be made by each patient's primary physician using current clinical standards, without input from quantitative analysis of the RT3D images. For patients who undergo cardiac catheterization, angiograms can be reviewed according to standard clinical practice by cardiologists not associated with the wall motion study. Lesions can be visually assessed and significant stenosis defined as a greater than 50% decrease in normal luminal diameter. Lesions can also be graded by digital quantitative vessel analysis (QVA).

Quantitative wall motion analysis can be performed as described above. The threshold 3DFS value taken to indicate clinically significant coronary artery disease can be initially set at 0.05 based on the pilot studies, then adjusted by plotting receiver operating characteristics (ROC) curves for different thresholds and selecting the 3DFS threshold that maximizes the area under the ROC curve.

Wall motion scoring can be conducted by expert cardiologists blinded to the experimental condition, using the standard sixteen-segment model and methods recommended by the American Society of Echocardiography. Wall motion analysis can also be conducted on MR image datasets using the same procedures described above for RT3D echocardiography data.

Five expert cardiologists can score fifty image datasets (50 baseline and 50 stress echocardiography images) from patients who underwent both coronary angiography and dobutamine echocardiography and forty image datasets (20 baseline, 20 stress) from patients who underwent both coronary angiography and dobutamine MRI. Each cardiologist can also manually segment each image dataset, and the resulting data can be fitted and analyzed as described above. Separate contingency tables can be constructed for each method (3DFS and scoring) and used to compute sensitivity, specificity, and accuracy and their confidence intervals for each method. The statistical significance of parameter differences between methods (3DFS vs. scoring) can be tested separately for MRI and RT3D images.

3DFS may provide a more accurate prediction of clinically significant coronary stenosis than wall motion scoring as indicated by statistically significant increases in sensitivity, specificity, and accuracy. This validation of 3DFS for detecting and localizing clinically significant coronary artery disease can impact clinical practice.

A difference between model and pilot experiments is the severity of the induced ischemia. While the model simulates a fully transmural ischemic region and the pilot experiments involved complete transient occlusion of individual coronary arteries, stress in a patient with limited coronary flow reserve produces a much smaller relative deficit in regional blood flow than complete coronary occlusion. In response, the threshold below which wall motion is considered "abnormal" may have to be varied in order to obtain an appropriate balance between sensitivity and specificity for coronary artery disease in the clinical studies.

The results of the wall motion analysis can depend in part on the quality of the acquired images, so variability in image quality is a potential source of error. However, one of the advantages of RT3D ultrasound for stress echocardiography is that acquisition from a single transducer position reduces dependence on sonographer skill compared to two-dimensional echo. It has been found that >94% of all segments may be visualized on RT3D contrast-enhanced dobutamine stress echo images, even in a patient population including numerous heart transplant recipients considered very difficult to image on echocardiography.

Engineers and physiologists have typically studied the mechanics of small regions of the heart using implanted sonomicrometers or radiopaque markers. Using these methods, it has been shown that when a region of the heart is contracting normally, it shortens as blood is ejected from the heart during systole, then stretches back to its original length as the heart fills with blood during diastole (FIG. 13A). When this region is suddenly deprived of blood flow (acute ischemia), it rapidly loses the ability to contract. It then behaves as a passive material, stretching as pressure and wall stress increase during diastolic filling and isovolumic contraction, then recoiling as wall stress drops during ejection and isovolumic relaxation (FIG. 13A). A consequence of these very different temporal patterns of deformation is that while shortening in normal myocardium can be adequately assessed by comparing images taken at end diastole and end systole, the amount of stretching in ischemic myocardium may be severely underestimated by such an analysis. Further, the temporal pattern of deformation can depend on the severity of ischemia and the size of the ischemic region. Therefore, if information from the full time course of contraction is available, the different temporal patterns may facilitate the tasks of distinguishing acutely ischemic from normal myocardium and estimating ischemic region size and severity.

Wall motion in an ischemic region arises from a complex combination of myocardial shortening or stretching, wall thickening, and displacement of adjacent myocardium. The resulting temporal patterns of deformation are complex and depend on both the size and severity of regional ischemia. These temporal patterns therefore contain information that may be used to better estimate ischemic region size, location, and severity. Based on what is known about the mechanics of regional ischemia, it is expected that only severely ischemic regions may display the rapid outward motion during isovolumic contraction illustrated in FIG. 13A. To gain a diagnostic advantage from this insight, computational modeling is used to capture the additional information available in fully four-dimensional wall motion data for use in defining ischemic region size and severity. In canine pilot data, a four-dimensional measure that was tested, local rate of inward/outward motion (dλ/dt), was a more specific indicator of severe regional ischemia than 3DFS (FIGS. 11A-C, 16C), suggesting that four-dimensional analysis may improve quantification of acute ischemia. FIG. 13C, for example, maps the rate of outward wall motion and identifies the ischemic region created by temporary occlusion of the left circumflex coronary artery.

Figure 14:
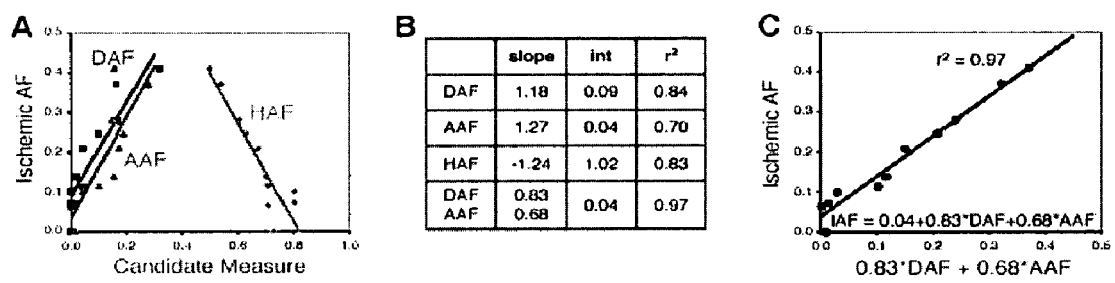
FIGS. 14A-C illustrate a regression-based approach to devising customized measures for quantification of regional ischemia in accordance with some embodiments of the disclosed subject matter.

Testing can include a computational phase and an experimental phase. The approach is illustrated in FIGS. 14A-C, using the data from the computational study described above in connection with FIGS. 8A-C. This approach defines customized measures that can provide accurate, robust predictions of the size and severity of acutely ischemic regions. A wide range of ischemic region locations, sizes, and severities can be simulated in a four-dimensional model of acute ischemia and a large pool of candidate wall motion measures can be screened. The fully four-dimensional models can allow for screening of a range of candidate measures that include, for example, maximal extent (maxFS) and rates (±dλ/dt) of motion, spatial gradients (dλ/dθ, dλ/dµ), and curvatures.

First, individual wall motion measures that have significant regression slopes against the size or severity of the simulated ischemic region can be identified. Then, multiple regression analysis can be used to determine what combinations of these measures gives the most accurate prediction of ischemic region size, location and severity across the entire set of simulations. Once appropriate combinations of four-dimensional measures have been identified, a fully four-dimensional analysis of the RT3D ultrasound images acquired during the experimental phase can be performed and the ability of these combinations to predict ischemic region size and severity measured independently by colored microsphere analysis can be tested.

End diastole and end systole were simulated for a range of ischemic region sizes and locations, and the fraction of the endocardial surface area displaying different levels of dysfunction was calculated and termed the dyskinetic area fraction (DAF), akinetic area fraction (AAF), and hypokinetic area fraction (HAF). For illustration purposes only, these three area fractions were treated as separate candidate measures. Each of these measures yielded slopes significantly different from zero when regressed against ischemic area fraction (IAF), and may therefore be used to predict IAF (FIGS. 14A-C). However, the slopes, intercepts, and $r^2$ values for these regressions were all different. The intercept on the IAF axis represents the threshold ischemic region size detectable using a particular measure. A strategy of giving priority to the measures with the smallest intercepts would suggest preferring AAF over DAF and excluding HAF. By multiple linear regression, both AAF and DAF made independent contributions to predicting ischemic area fraction (P<0.001), with the regression equation $IAF_{pred}$=0.04+0.83*DAF+ 0.68*AAF achieving an $r^2$ value of 0.97 against IAF, providing much better prediction than either measure alone (FIGS. 14A-C). The tolerance for AAF and DAF was 0.64, suggesting that these measures were not strongly collinear.

FIGS. 14A-C illustrates the regression-based approach to devising customized measures for quantification of regional ischemia. FIG. 14A demonstrates that wall-motion-based measures of the fraction of the endocardial surface area exhibiting dyskinesis (DAF), akinesis (AAF), and hypokinesis (HAF) can each be employed in single linear regression to predict the fraction of the endocardial surface that was ischemic in the model simulation. FIG. 14B provides coefficients for regressions in FIG. 14A (int=intercept on IAF axis), which illustrate that AAF is most sensitive to small ischemic regions (smallest intercept). FIG. 14C demonstrates that a multiple linear regression against DAF and AAF yields an equation that predicts IAF very accurately across the entire range of simulated ischemic region sizes and locations.

For the modeling work described above, anatomically detailed models can be adapted that incorporate measured geometry, fiber architecture, and Purkinje fiber networks based on exhaustive measurements in the canine heart. During diastole, passive myocardium is modeled as a nonlinear, orthotropic, nearly incompressible material. During systole, electrical impulse propagation throughout the heart is simulated and tension generation is initiated locally when the local myocyte transmembrane potential reaches a critical threshold. Tension generation is governed by local intracellular calcium concentrations and exhibits appropriate dependence on local fiber length and on global inotropic state. The entire left ventricular model can then be coupled to a Windkessel model to simulate the arterial tree. Acute ischemia can be incorporated into four-dimensional model, defining a nodal field variable that crosses zero at the ischemic region boundary, with negative values indicating ischemic regions and triggering a local increase in the calcium concentration required to achieve 50% maximal activation ($C_{50}$). As illustrated in FIGS. 8A-C, by manipulating this field variable the size and location of the simulated ischemic region can be adjusted as needed for the simulations. Ischemia of varying severity can be simulated by manipulating the calcium sensitivity parameter $C_{50}$ in simulated ischemic regions and these simulations can be verified by comparing model strains to experimental sonomicrometry data.

The endocardium can be treated as a finite element mesh evolving in time. Parameter values, namely λ and spatial derivatives of λ, defined at spatiotemporal nodes allow for a compact representation of the complex shape of the endocardial surface throughout the cardiac cycle. To interpolate λ at other locations or times, basis functions are evaluated to determine the relative contribution of the nodal parameters. In each direction of the spatial domain, cubic Hermite basis functions are used to ensure $C^1$ continuity. The temporal domain can be represented by a single Lagrange element. In this dimension, cubic Lagrange basis functions adequately describe the behavior of λ throughout the simulated cardiac cycle (see, e.g., FIG. 6D). For spatial coordinates, $\xi_1$ and $\xi_2$, and temporal coordinate, $\xi_t$, the governing equation is expressed as:

$$\lambda(\xi_1,\xi_2,\xi_t)=\Lambda_0(\xi_1,\xi_2)L_0(\xi_t)+\Lambda_{1/3}(\xi_1,\xi_2)L_{1/3}(\xi_t)+\Lambda_{2/3}(\xi_1,\xi_2)L_{2/3}(\xi_t)+\Lambda_1(\xi_1,\xi_2)L_1(\xi_t) \quad (6)$$

where $\Lambda_x$ represents the finite element mesh at the temporal node corresponding to it $\xi_t$=x and is computed according to Hashima et al. The fitting process calculates the set of nodal parameters that minimizes the difference between the spatiotemporal data and the resulting endocardial surface in the least squares sense.

Based on these tests, a small, severely ischemic region and a large, mildly ischemic region may both display similar areas of abnormal 3DFS. However, based on what is known about the mechanics of regional ischemia, only severely ischemic regions may display the rapid outward motion during isovolumic contraction illustrated in FIG. 13A. Therefore, combinations of 3DFS-based measures and dλ/dt-based measures may be able to predict both ischemic region size and ischemic region severity. For example, subtracting some fraction of the area showing early outward motion from the total abnormal area may tend to correct size estimates, reducing the estimate for small, severely ischemic regions. The model analysis may identify multiple combinations of two to three measures that provide near-perfect prediction of model ischemic region size or severity. When these combinations are applied to the experimental 4D data, at least one combination identified from the modeling may predict ischemic region size and at least one may predict severity with an $r^2 \geqq 0.90$, although the weights in the resulting best-fit regression may differ from those for model data.

The analysis methods described herein may improve accuracy in deciding which patients need to proceed to a more invasive procedure (e.g., cardiac catheterization) and which patients can be safely spared further tests and procedures.

Example 2

This example illustrates a model-based approach to designing wall motion measures using finite element models of altered cardiac activation to screen for wall-motion-based measures of synchrony of contraction. In connection with this, results indicate that early systolic events and specifically early systolic rates of endocardial motion may be the best wall-motion-based indicators of synchrony of contraction, thereby confirming that fully four-dimensional wall motion analysis in accordance with the methods described herein may be useful for this clinical application.

This example relates to the development of clinically useful quantitative measures of left ventricular wall motion. In many clinical situations, a physician needs to assess the function of the left ventricle (LV), the main pumping chamber of the heart. When the goal is to assess pump function of the LV as a whole (global function), analysis is usually based on simple hemodynamic data such as pressures and volumes. However, when the goal is to assess differences in function in various regions of the LV (regional function), more sophisticated methods are required.

Engineers and clinicians have historically taken divergent approaches to assessment of regional left ventricular function. Using implanted measuring devices such as sonomicrometers and radiopaque markers, engineers have studied regional differences in strain in the heart wall and related these deformation patterns to the underlying physiology and pathophysiology. By contrast, cardiologists have learned to make diagnoses based on qualitative assessment of the patterns of motion of the endocardial surface as visualized in ultrasound images of the heart (echocardiograms).

In accordance with the methods described herein, the motion of the left ventricular endocardium can be parameterized in space and time to obtain a complete, patient-specific mathematical description of left ventricular wall motion. Any number of measures of wall motion can be computed from this parameterization related to particular diagnostic goals.

This example is related to a wall-motion-based measure of left ventricular asynchrony. This example is clinically relevant because increasing numbers of patients with heart failure are now being treated with cardiac resynchronization therapy, in which implanted multi-lead pacemakers are used to modify the pattern of contraction of the heart. A quantitative wall-motion-based measure of contraction synchrony may facilitate bedside and in-office optimization of pacemaker settings under echocardiographic visualization. In connection with developing such a measure, finite element models of cardiac contraction driven by two different activation patterns were employed to screen for wall motion measures that may distinguish between these cases.

A first computational method employed in connection with this example was a computational electromechanical model. A three-dimensional finite element model of the canine left and right ventricular anatomy with detailed myofiber and sheet architecture was based on measurements in the canine heart. Briefly, the passive myocardium was treated as a non-linear, orthotropic, and nearly incompressible material, with active stresses being a function of peak intracellular calcium concentration, sarcomere length, and time. The LV endocardium was constrained at the base to allow cavity expansion, but not longitudinal displacement, to simulate the effects of the relatively stiff annuli of the valves. Isovolumic contraction and relaxation phases were modeled by introducing constraints to prevent significant volume changes. Coupling the ventricles to two-element resistance-compliance Windkessel models of the time-varying pulmonary and arterial input impedances allowed ventricular pressures to be calculated during ejection. Right and left ventricular cavity pressures were assumed to be uniform on the endocardium, with no pressure applied to the epicardium.

Electrical propagation in the heart normally begins at the sinoatrial (SA) node, located on the right atrium. The impulses eventually reach the atrioventricular (AV) node, located near the base of the right ventricle. From the AV node, the electrical impulses spread through an extensive network of conducting fibers, known as Purkinje fibers, which connect to the sub endocardium of both ventricles, and then through the myocardium itself. LV contraction, which follows electrical activation, proceeds quickly from apex to base, squeezing blood through the aorta. Left bundle branch block (LBBB) is an impairment in which electrical conduction in the left bundle branch, which includes the Purkinje fibers, is blocked. During LBBB, spread of electrical activation depends more on slow propagation through the myocardium and less on rapid propagation through the Purkinje network. Activation takes much longer than normal and creates large disparities in activation time among different regions of the LV. The resulting contraction is less synchronous and less efficient than for a normally activated LV.

Figure 15:
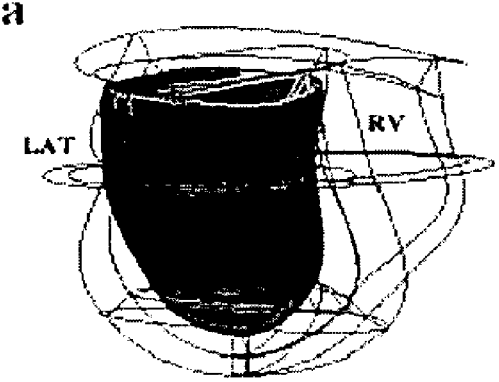
FIGS. 15A-D illustrate a finite-element model of the left ventricle capable of simulating different patterns of electrical activation in the left ventricle that was used to test strategies for diagnosing left ventricular asynchrony in accordance with some embodiments of the disclosed subject matter.
Figure 15:
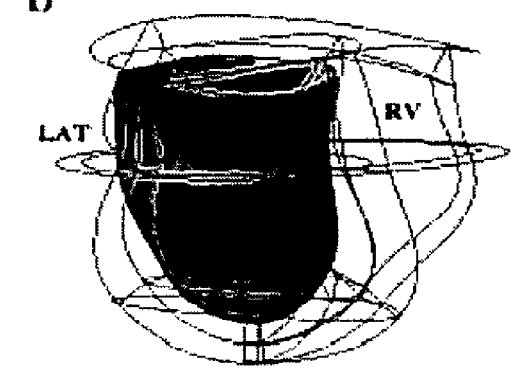
Figure 15:
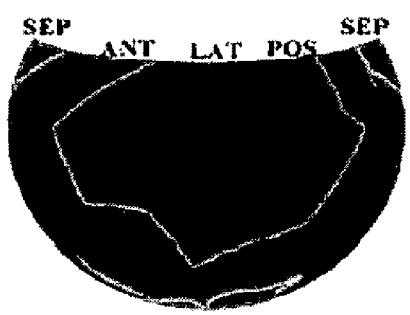
Figure 15:
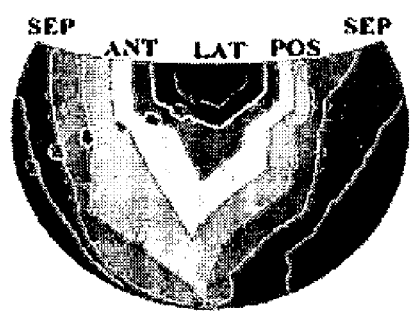

Biventricular (BiV) pacing (i.e., electrical stimulation of the left and right ventricles using a pacemaker) has been shown to improve systolic function in patients with LBBB. Electrical propagation during LBBB was modeled by applying an initial stimulus at the right bundle branch of a simulated Purkinje network embedded in the model. To model BiV pacing, stimuli were applied simultaneously to the LV mid-lateral epicardium and the right ventricular free wall epicardium, typical pacing sites used clinically to treat LBBB. FIGS. 15A-D illustrate the spread of electrical stimuli on the LV endocardial surface. The wireframe in FIGS. 15A and B outline the biventricular finite element model with the RV cavity and LV lateral wall labeled. Activation time for the LV endocardium is displayed as a shaded surface. FIGS. 15C and D are Hammer projections mapping activation time (in ms) to circumferential and longitudinal position. In FIGS. 15C and D, contour boundaries are spaced by 10 ms, and the septal (SEP), anterior (ANT), lateral (LAT), and posterior (POS) regions are labeled. The propagation of electrical excitation and recovery in the myocardium was modeled using a three-dimensional version of the cable equation for electrophysiology, which is a reaction-diffusion equation with the diffusion tensor representing the anisotropic intracellular conductivity of the myocardial syncytium. An extra diagonal diffusion tensor was added to represent conductivity along the Purkinje fibers.

Figure 16:
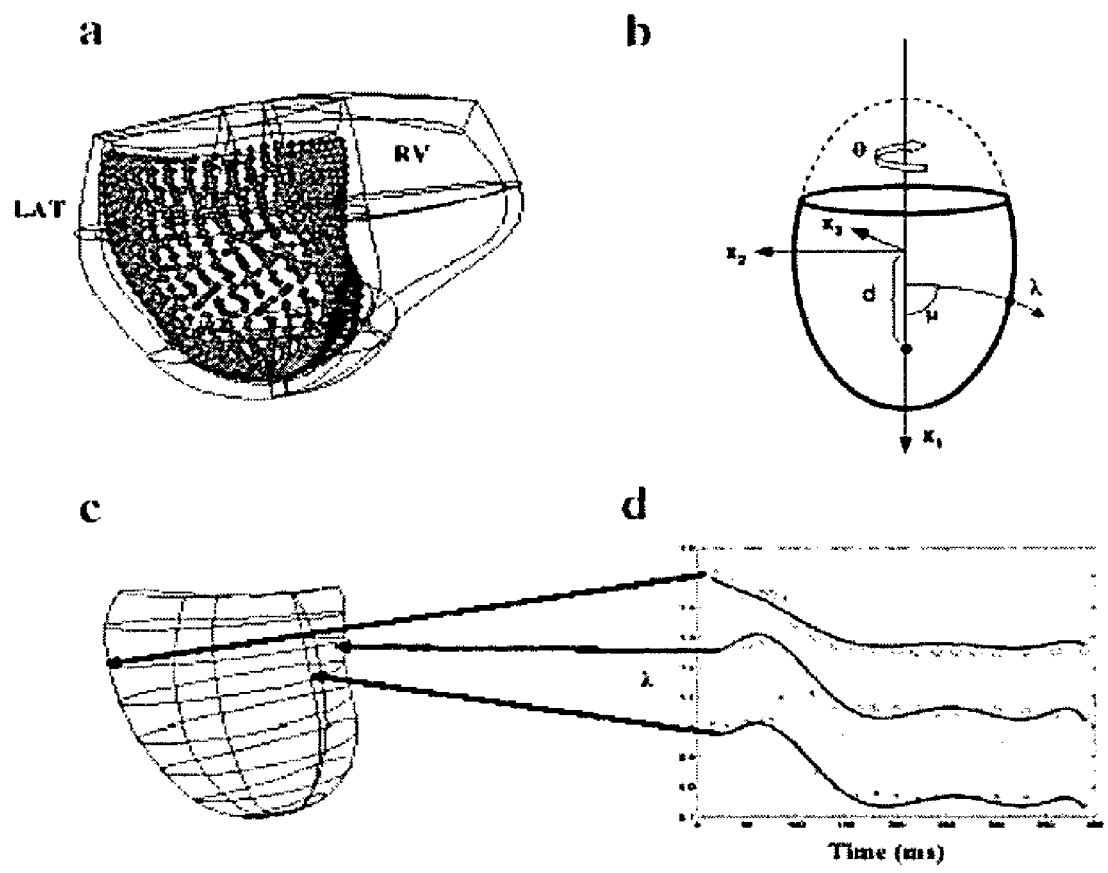
FIGS. 16A-D illustrate the fitting of endocardial surface data from finite element models in accordance with some embodiments of the disclosed subject matter.

The solution of each pacing model was a series of twenty finite element meshes representing ventricular geometry at various time points during isovolumic contraction, systolic ejection, and isovolumic relaxation. Cartesian coordinates of 1200 surface points extracted from each of these finite element meshes served as input for the fitting procedure described below. FIGS. 16A-D illustrate the fitting of endocardial surface data from finite element models. FIG. 16A shows an example cloud of LV endocardial surface points superimposed on the corresponding finite element mesh (wire frame). Each point was converted to prolate spheroidal coordinates, allowing its location to be expressed in terms of one normalized distance along an arc ($\lambda$) and two angular coordinates indicating circumferential ($\theta$) and longitudinal ($\mu$) position. FIG. 16B illustrates the prolate spheroidal coordinate system used to define points on the LV endocardial surface. In this coordinate system, the length scale is determined by a focal distance (d in FIG. 16B), which was set to 15 mm so that the $\lambda$=1 surface yielded a good initial approximation of the LV endocardium. FIG. 16C illustrates a finite element mesh of the LV endocardial surface obtained by fitting the points shown in FIG. 16A. FIG. 16D illustrates the behavior of coordinate $\lambda$ over time for three sample positions on the finite element mesh in FIG. 16C. Curves represent behavior captured by the four-dimensional spatiotemporal fit, while symbols plot the $\lambda$ values obtained via three-dimensional fits to data for individual time points.

A second computational method employed in connection with this example was spatiotemporal interpolation using basis functions. For each data point, the coordinate $\lambda$ was expressed as an algebraic function of circumferential and longitudinal position and time. Hence, the LV endocardial surface was treated as a finite element mesh deforming continuously in time. Parameter values, namely $\lambda$ and spatial derivatives of $\lambda$, defined at spatiotemporal nodes allowed for a compact representation of the complex shape of the endocardial surface throughout the cardiac cycle.

Interpolation of $\lambda$ throughout the spatiotemporal domain made use of hybrid tensor product basis functions. In each direction of the spatial domain, cubic Hermite basis functions were used to ensure $C^1$ continuity, yielding smooth transitions between elements. These one-dimensional functions are given by $$H^0_0(\xi) = 1 - 3\xi^2 + 2\xi^3$$

$$H^1_0(\xi) = \xi(\xi-1)^2$$

$$H^0_1(\xi) = \xi^2(3-2\xi)$$

$$H^1_1(\xi) = \xi^2(\xi-1) \quad (7)$$

where $\xi$ is a generic normalized local element coordinate between 0 and 1. $H^x_0$ and $H^x_1$ weight values of $\lambda$ (when x=0) or $\partial\lambda/\partial\xi$ (when x=1) at nodes corresponding to $\xi$=0 and $\xi$=1, respectively. The temporal domain was represented by a single element using a seventh-order Lagrange polynomial basis function, which was found to adequately describe the behavior of $\lambda$ throughout the simulated cardiac cycle and sufficiently minimize RMS error in B. In general, these functions are written as $$L_x(\xi) = \Pi^7_{y=0,y\neq x}(\xi-\xi_y)/\Pi^7_{y=0,y\neq x}(\xi_x-\xi_y) \quad (8)$$

where x is an integer between 0 and 7 and $L_x$ weights $\lambda$ at the node corresponding to $\xi$=x/7. Using a seventh-order Lagrange basis requires that $\lambda$ be specified at each of eight nodal locations ($\xi$=0, 1/7, 2/7, 3/7, 4/7, 5/7, 6/7, and 1). No derivatives of $\lambda$ with respect to time are needed.

Tensor products of the one-dimensional basis functions in space and time were constructed to yield a mixed bicubic Hermite (space), seventh-order Lagrange (time) interpolation scheme. For spatial coordinates, $\xi_1$ and $\xi_2$, and temporal coordinate, $\xi_t$, the governing equation is expressed as $$\lambda(\xi_1,\xi_2,\xi_t) = \Lambda_0(\xi_1,\xi_2)L_0(\xi_t) + \Lambda_1(\xi_1,\xi_2)L_1(\xi_t) + \Lambda_2(\xi_1,\xi_2)L_2(\xi_t) + \Lambda_3(\xi_1,\xi_2)L_3(\xi_t) + \Lambda_4(\xi_1,\xi_2)L_4(\xi_t) + \Lambda_5(\xi_1,\xi_2)L_5(\xi_t) + \Lambda_6(\xi_1,\xi_2)L_6(\xi_t) + \Lambda_7(\xi_1,\xi_2)L_7(\xi_t) \quad (9)$$

where $\Lambda_x$ represents the degrees of freedom (DOFs) of the finite element mesh at the temporal node corresponding to $\xi_t$=x/7. Each $\Lambda_x$ is calculated as $$\Lambda_x(\xi_1,\xi_2) = H^0_0(\xi_1)H^0_0(\xi_2)\lambda_{x,1} + H^0_0(\xi_1)H^0_1(\xi_2)\lambda_{x,3} + H^0_1(\xi_1)H^0_1(\xi_2)\lambda_{x,4} + H^1_0(\xi_1)H^0_0(\xi_2)(\partial\lambda/\partial\xi_1)_{x,1} + H^1_0(\xi_1)H^0_1(\xi_2)(\partial\lambda/\partial\xi_1)_{x,3} + H^1_1(\xi_1)H^0_0(\xi_2)(\partial\lambda/\partial\xi_1)_{x,2} + H^1_1(\xi_1)H^0_1(\xi_2)(\partial\lambda/\partial\xi_1)_{x,4} + H^0_0(\xi_1)H^1_0(\xi_2)(\partial\lambda/\partial\xi_2)_{x,1} + H^0_1(\xi_1)H^1_0(\xi_2)(\partial\lambda/\partial\xi_2)_{x,2} + H^0_0(\xi_1)H^1_1(\xi_2)(\partial\lambda/\partial\xi_2)_{x,3} + H^0_1(\xi_1)H^1_1(\xi_2)(\partial\lambda/\partial\xi_2)_{x,4} + H^1_0(\xi_1)H^1_0(\xi_2)(\partial^2\lambda/\partial\xi_1\partial\xi_2)_{x,1} + H^1_1(\xi_1)H^1_0(\xi_2)(\partial^2\lambda/\partial\xi_1\partial\xi_2)_{x,2} + H^1_0(\xi_1)H^1_1(\xi_2)(\partial^2\lambda/\partial\xi_1\partial\xi_2)_{x,3} + H^1_1(\xi_1)H^1_1(\xi_2)(\partial^2\lambda/\partial\xi_1\partial\xi_2)_{x,4} \quad (10)$$

where $\lambda_{x,y}$, $(\partial\lambda/\partial\xi_1)_{x,y}$, $(\partial\lambda/\partial\xi_2)_{x,y}$, and $(\partial^2\lambda/\partial\xi_1\partial\xi_2)_{x,y}$ are parameter values at spatial node y and temporal node x of the four-dimensional finite element mesh. Using the analytic expressions above, derivatives of $\lambda$, such as $\partial\lambda/\partial\xi_1$ and $\partial\lambda/\partial\xi_1$, are interpolated by simply differentiating the appropriate basis functions.

The accuracy of the interpolation presented above depends on how well the nodal parameter values describe the shape of the endocardial surface throughout time. The fitting process calculates the optimal set of nodal parameters which minimizes the difference between the spatiotemporal data and the resulting endocardial surfaces in the least-squares sense. Hence, the nodal $\lambda$, $\partial\lambda/\partial\xi_1$, $\partial\lambda/\partial\xi_2$, and $\partial^2\lambda/\partial\xi_1\partial\xi_2$ values were considered the DOFs for this procedure. It is important to realize that fitting data in space and time will yield eight such sets of DOFs, one for each temporal node, when using a seventh-order Lagrange temporal basis. These were represented by $\Lambda_{0-7}$ in equation (9).

To start, the four-dimensional surface is initially defined as a static simple ellipsoid by setting $\lambda$=1 and all $\lambda$ derivatives=0 for all nodes in space and time. For each spatiotemporal data point, ($\lambda$, $\xi$, $\theta$, $t)_d$, the local temporal coordinate, $\xi_t$, is computed by normalizing $t_d$ by the duration of the simulated cardiac cycle (in ms). Local spatial coordinates, $\xi_1$ and $\xi_2$, are determined by $\Xi_d$, $\theta_d$, and the element boundaries of the initial mesh. The difference in $\lambda$ between the data point and the initial four-dimensional surface is computed as $\lambda_d - \lambda_i(\xi_1, \xi_2, \xi_t)$, where $\lambda_i$ is interpolated using the nodal parameters defined initially. Ideally, if the solution DOFs are a perfect representation of the data, $\lambda_d$ can be rewritten as $$\lambda_d(\xi_1,\xi_2,\xi_t) = \langle H(\xi_1,\xi_2)L(\xi_t), D_S \rangle \quad (11)$$

where $H(\xi_1, \xi_2)L(\xi_t)$ is shorthand for the products of the bicubic Hermite and seventh-order Lagrange basis functions evaluated at $(\xi_1, \xi_2)$ and $\xi_t$, respectively. $D_S$ denotes the solution DOFs and $\langle x, y \rangle$ performs the dot product of x and y. Similarly, if $D_i$ collectively represents the degrees of freedom (nodal parameters) for the initial four-dimensional mesh, then $\lambda_i$ can be expressed as $$\lambda_i(\xi_1,\xi_2,\xi_t) = \langle H(\xi_1,\xi_2)L(\xi_t), D_i \rangle \quad (12)$$

and hence, $$\lambda_d(\xi_1,\xi_2,\xi_t) - \lambda_i(\xi_1,\xi_2,\xi_t) = \langle H(\xi_1,\xi_2)L(\xi_t), D_S \rangle - \langle H(\xi_1,\xi_2)L(\xi_t), D_i \rangle \quad (13)$$

or $$(\lambda_d - \lambda_i)(\xi_1,\xi_2,\xi_t) = \langle H(\xi_1,\xi_2)L(\xi_t), D_S - D_i \rangle \quad (14)$$

For n data points and k DOFs (n>>k), the above equation can be vectorized to form an over-determined linear system. Let b=$[\lambda_d-\lambda_i]$ be the n×1 vector of known residuals in $\lambda$;

A=[HL] be the n×k matrix of bicubic Hermite-cubic Lagrange basis function products; and x=$[D_S-D_i]$ be the k×1 vector of unknown residuals of the DOFs. The resulting system, b=A x, is solved for x using the pseudo-inverse as $$x = (A^T A)^{-1} A^T b \quad (15)$$

and is equivalent to the least-squares solution of the matrix problem. Because x=$[D_S-D_i]$ is the vector of nodal parameter residuals, the desired solution DOF vector is simply $D_S$=x+$D_i$.

The spatiotemporal fits corresponding to BiV and LBBB pacing resulted in RMS errors in $\lambda$ of 0.021 and 0.015, respectively, which correspond to fitting errors of less than 3% for $\lambda$ values of order 1. These were consistent with the RMS errors calculated for three-dimensional fits of data from individual time points, indicating that the spatiotemporal fits did not compromise the accuracy of the finite element representation of the endocardial surface. Overall, these errors were considerably less than the errors associated with creating the original model surface from anatomical measurements. For both pacing scenarios, the least-squares algorithm required 50 MB of main memory and ran for approximately 35 minutes on a Silicon Graphics Origin 2 workstation running MATLAB 6.5. A total of 1728 degrees of freedom were needed to describe the dynamic LV surface and 23 MB, almost half the total memory usage, was required to store the 1728×1728 pseudo-inverse matrix, $(A^T A)^{-1}$ from equation (15).

Figure 17:
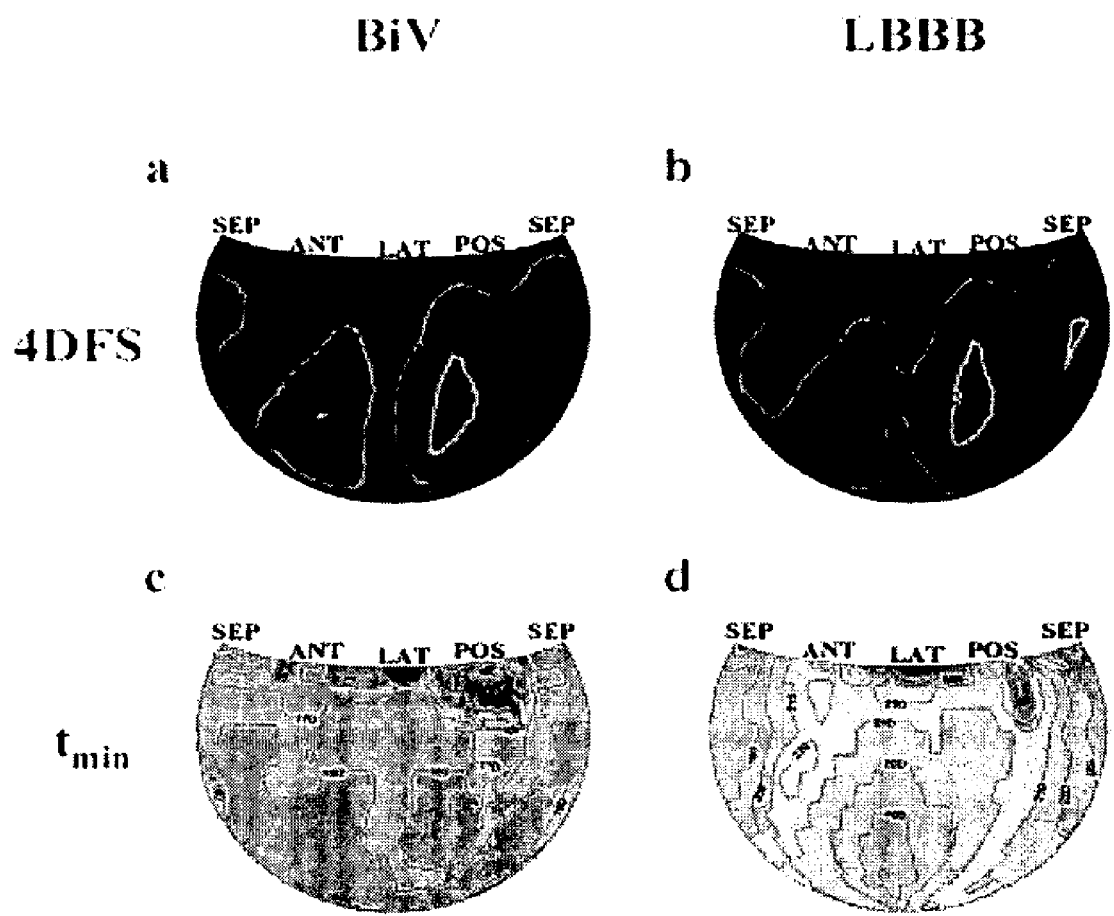
FIGS. 17A-D illustrate the effect of asynchrony on late systolic wall motion in accordance with some embodiments of the disclosed subject matter.

In connection with detecting asynchrony from wall motion patterns, one area considered was the extent of maximal endocardial excursion. Since the physiologic disadvantage of left ventricular asynchrony is that much of the energy expended by any one region is wasted in stretching other regions that have completed or have not yet begun contraction, it was expected that the model of left bundle branch block (LBBB) might demonstrate less ejection against the same simulated arterial tree than the model of biventricular (BiV) pacing. A wall motion measure was defined that would quantify the maximal amount of inward motion towards the central axis achieved by each region of the endocardial surface, starting from end-diastole: four-dimensional fractional shortening, 4DFS=$(\lambda_{ED}-\lambda_{MIN})/\lambda_{ED}$. This measure is similar to the measure three-dimensional fractional shortening (3DFS) described herein, except that it does not assume that the maximal excursion of any point on the surface occurs at the same time as global end-systole. The distribution of regional 4DFS values was remarkably similar in both LBBB and BiV models. Globally, reduced efficiency of contraction in the LBBB model was reflected in lower systolic pressures rather than depressed stroke volume. FIGS. 17A-D illustrate the effect of asynchrony on late systolic wall motion. FIGS. 17A and B display Hammer maps of four-dimensional fractional shortening, 4DFS=$(\lambda_{ED}-\lambda_{MIN})/\lambda_{ED}$, for BiV and LBBB pacing scenarios, respectively. Contour boundaries are separated by 10% increments. FIGS. 17C and D display corresponding Hammer maps for $t_{min}$, the time at which $\lambda$ reaches its minimum value, with contour boundaries separated by 10 ms. Neither 4DFS nor $t_{min}$ reflected the very different activation patterns in the two models.

In connection with detecting asynchrony from wall motion patterns, another area considered was the timing of maximal endocardial excursion. Although each region had apparently reached a similar minimum $\lambda$ value (maximal inward excursion) under the two different simulated pacing protocols, it was expected that the time at which this local minimum point was achieved would differ between the two models. The time to minimum $\lambda$ ($t_{min}$) was proposed as a measure and expected that the distribution of this measure would parallel the distribution of electrical activation times in each model. After computing and mapping this measure (FIGS. 17C and D), it was found that the average time from end diastole to minimum $\lambda$ was substantially longer in the LBBB model, consistent with the greater average activation time relative to end diastole (FIGS. 15A-D). However, the range of $t_{min}$ values across the endocardial surface was narrow in the LBBB model (190-220 ms, compared to 160-180 ms for BiV). This result suggested that while the average time from pacing stimulus to minimum $\lambda$ may contain some useful information, $t_{min}$ is relatively insensitive to the activation pattern and therefore may not be a promising wall-motion-based measure of asynchrony.

Figure 18:
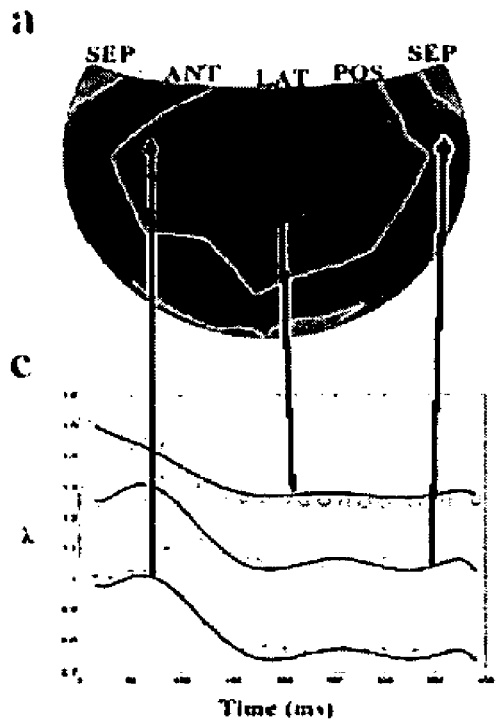
FIGS. 18A-F illustrate the effect of asynchrony on early systolic wall motion in accordance with some embodiments of the disclosed subject matter.
Figure 18:
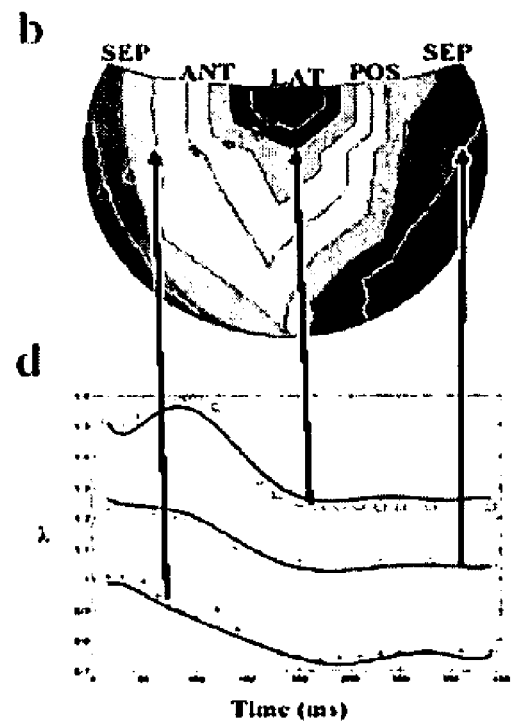
Figure 18:
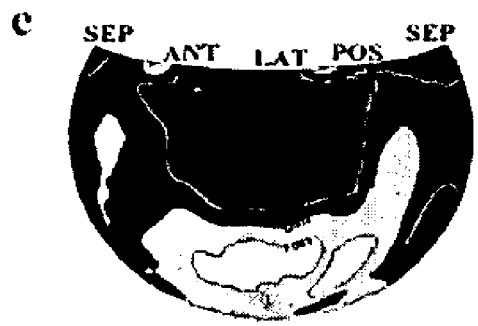
Figure 18:
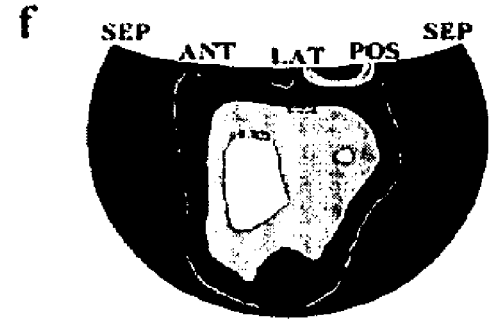

In connection with detecting asynchrony from wall motion patterns, yet another area considered was endocardial motion during early systole. During asynchronous activation, regions that are activated early initially contract at the expense of regions that are not yet activated. Therefore, an alternate strategy for identifying asynchronous activation may be the simultaneous presence of regions of shortening and stretching during early systole. With implanted markers or magnetic resonance tagging, stretching and shortening can be quantified directly. Wall motion analysis cannot identify stretching directly, but can look for outward bulging (dyskinesis) that is associated with local passive systolic stretching in certain situations and should contrast sharply with the inward systolic wall motion associated with normal contraction. The rate of change in $\lambda$, $\partial\lambda/\partial t$, was computed and it was found that early-activated regions moved inward immediately, while late-activated regions moved initially outward, indicating local bulging (FIGS. 18C and D). Shaded maps of maximum systolic $\partial\lambda/\partial t$ (FIGS. 18E and F) reveal the regions of local bulging corresponding to late activation. These maps were similar to the maps of activation times for both models (FIGS. 18A and B).

Figure 19:
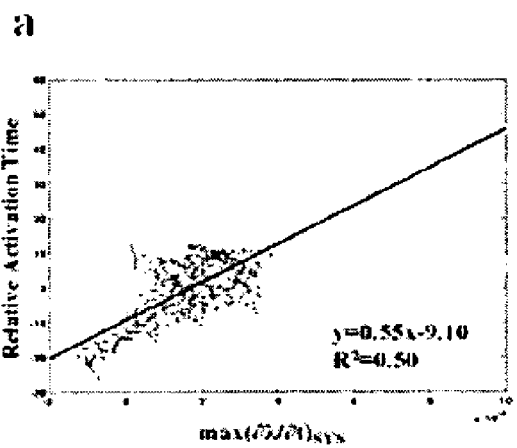
FIGS. 19A-B illustrate the relationship between activation time and maximum systolic $\partial\lambda/\partial t$ in accordance with some embodiments of the disclosed subject matter.
Figure 19:
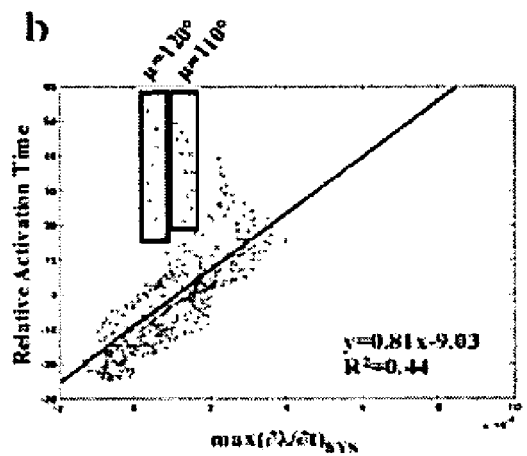

In the case of asynchrony, it was determined how accurately a measure such as maximum systolic $\partial\lambda/\partial t$ can predict an established measure such as activation time. Regressions of activation time against maximum systolic $\partial\lambda/\partial t$ showed $R^2$ values of about 0.5, with similar best-fit regression lines for points interpolated from the fits to the two models. In particular, FIGS. 19A-B illustrate the relationship between activation time and maximum systolic $\partial\lambda/\partial t$. As shown, activation time relative to mean, $t_{act}-t_{avg}$, correlated reasonably well with maximum systolic $\partial\lambda/\partial t$ for BiV (FIG. 19A) and LBBB (FIG. 19B) models. The relationship between these parameters breaks down near the base ($\mu=120°$ and $\mu=110°$) for the LBBB model. A possible explanation is that the basal boundary conditions, intended to simulate the fibrous valve ring tissue, restricted early systolic outward motion of late-activated myocardium near the base. Adding point location ($\Xi$ and θ) to the regression equations did not substantially improve the fit to the BiV model data, but did improve the fit to the LBBB model data, because most of the points that deviated substantially from the initial best-fit line were located at the base (FIGS. 19A-B). Due to the relatively low correlation coefficient values for maximum systolic $\partial\lambda/\partial t$, an alternate candidate measure of outward endocardial wall motion was considered. The maximal amount of outward motion during systole was calculated as $\lambda_{max}-\lambda_{ED}$. This measure was strongly correlated with maximum systolic $\partial\lambda/\partial t$ ($R^2$=0.82), showing that it does not provide much independent information, and its relationship to activation time was similar in the LBBB model and weaker in the BiV model. This measure is unlikely to represent a better wall-motion-based measure of asynchrony than maximum systolic $\partial\lambda/\partial t$.

The approaches to model-driven development of new wall motion measures may be subject to certain limitations that are described as follows. First, because wall motion analysis typically consists of comparing surfaces imaged at different times during the cardiac cycle rather than tracking identifiable material points over time, regional strains may not be readily computed and some aspects of ventricular motion known to be sensitive to altered activation or ischemia, such as torsion and wall thickening, may not be easily quantifiable. The limitations of wall-motion-based analysis may be offset by the broad accessibility to echocardiography at the bedside and the ability to tap directly into concepts with which the cardiologist is already familiar.

Second, model-based development can be misleading if the model does not accurately represent relevant aspects of the underlying anatomy and physiology. For example, despite poor synchrony in the LBBB model, it was found that ejection was essentially unchanged. Efficiency of contraction was depressed, but was apparent primarily as decreased systolic pressure generation rather than decreased stroke volume compared to the BiV model. It seems likely that this result depends, at least in part, on the choice of parameters for the Windkessel model, so it may be important to test the sensitivity of the results to the choice of these parameters and to verify the pressure-volume behavior of these two models against experimental data. In the iterative process of alternating between model experiments and clinical or animal studies, the models are important in guiding the choice of experiments and reducing their number by focusing attention on the parameters that are fundamental to a particular question. Another example of this is the finding that the relationship between maximum systolic $\partial\lambda/\partial t$ and activation time broke down at the base in the LBBB model. An explanation for this may be that the basal boundary conditions, intended to simulate the fibrous valve ring tissue at the base of the ventricles, restricted early systolic outward motion of late-activated myocardium near the base. The extent to which experiments confirm this specific aspect of model behavior may be important to determine, because it is possible that physical constraints at the ventricular base may pose a fundamental physical limit to wall-motion-based detection of base-to-apex differences in synchrony of contraction.

The papillary muscles and endocardial trabeculae present in the LV are not included in the finite element model employed in this example. Their absence may potentially impact the analysis in two ways. First, the absence of these structures may render the model and its wall motion less realistic. Since papillary muscles have been shown to play an important role in LV ejection and to affect deformation near their insertions in the wall, their inclusion may improve the match between model and actual wall motion near the papillary muscle insertions. Second, the absence of the papillary muscles in the model may directly alter the fitted λ values and the wall motion maps obtained, artificially increasing λ values where the papillary muscles would have been. This omission may serve to align the analysis more closely with current standards for clinical echocardiographic analysis, which ignore papillary muscles and trabeculations. These structures are intentionally excluded by cardiologists during manual tracing of the endocardial border for volume calculations and 2D wall motion analysis.

A final caveat concerns the regressions shown in FIGS. 19A-B. It is unclear how statistically independent to consider points sampled from the endocardial surface of a complex finite element model. While the motion of immediately adjacent points is clearly not independent, points on opposite sides of the model are essentially independent from one another except to the extent that the motion of both depends on overall hemodynamics. These same issues confound experimental and clinical analysis of the motion of points on the endocardial surface. Statistically, it is safer to compare the motion of a particular point on the surface across a number of different model runs or experiments and ask whether activation time and a particular wall motion measure are well-correlated across several independent experiments. However, keeping in mind the limitations, plots like those in FIGS. 19A-B can still be helpful at the modeling stage in screening for candidate measures likely to show strong covariance and in identifying specific questions to be addressed during experimental validation, such as the impact of basal boundary conditions discussed above.

This example illustrates a model-based approach to developing clinically useful quantitative measures of left ventricular wall motion. Methods for parameterizing endocardial surface motion in four dimensions are described and measures of endocardial wall motion for use in quantifying asynchrony during cardiac resynchronization therapy have been evaluated. While late systolic measures of left ventricular contraction and timing may provide useful information about contraction synchrony, early systolic motion was the most sensitive to activation pattern. In addition, it was found that the rate, rather than the amount, of this motion appears to be the more promising candidate measure of contraction. This finding illustrates the potential value of the fully four-dimensional approach to parameterization described herein. The model-based approach to development of wall motion measures described herein has the benefit that a wide range of conditions can be simulated inexpensively and quickly, so that subsequent experimental validation can focus on the most promising measures using a reduced number of appropriately designed experiments. In particular, maximum systolic $\partial\lambda/\partial t$ as a measure of asynchrony may be further validated by acquiring MRI or ultrasound images using nonstandard protocols that enhance temporal resolution during early systole. The model-based approach described herein also facilitates exploration of the underlying physiology, for example, the finding that maximum systolic $\partial\lambda/\partial t$ may decouple from activation time near the base due to physical constraints imposed by the valve rings.

It will be understood that the foregoing is only illustrative of the principles of the invention, and that various modifications can be made by those skilled in the art without departing from the scope and spirit of the invention.

What is claimed is:

1. A method for providing diagnostic information using endocardial surface data for a patient's heart, the method comprising:

receiving endocardial surface data for the left ventricle of a heart, wherein the endocardial surface data represents the endocardial surface of the left ventricle at multiple times over a heartbeat, the multiple times comprising end diastole and end systole of the heartbeat, and wherein the endocardial surface data is obtained using a volumetric imaging application;

generating a representation in prolate spheroidal coordinates of the endocardial surface of the left ventricle at end diastole and end systole using the endocardial surface data, wherein the prolate spheroidal coordinates comprise a longitudinal angular coordinate μ, a circumferential angular coordinate θ, and a coordinate λ as a function of longitudinal angular coordinate μ and circumferential angular coordinate θ, and wherein $\lambda_{ED}$ represents the value of coordinate λ at end diastole and $\lambda_{ES}$ represents the value of coordinate λ at end systole; and computing three-dimensional fractional shortening ("3DFS") of the left ventricle as 3DFS=$(\lambda_{ED}-\lambda_{ES})/\lambda_{ED}$, wherein the three-dimensional fractional shortening identifies an ischemic region of the left ventricle.

2. The method of claim 1, further comprising:
providing an indication of the three-dimensional fractional shortening on a map of the left ventricle, such that the ischemic region of the left ventricle is identified on the map.

3. A method for providing diagnostic information using endocardial surface data for a patient's heart, 'the method comprising:
receiving endocardial surface data for the left ventricle of a heart, wherein the endocardial surface data represents the endocardial surface of the left ventricle at multiple times over a heartbeat, and wherein the endocardial surface data is obtained using a volumetric imaging application;

generating a representation in prolate spheroidal coordinates of the endocardial surface of the left ventricle at least a portion of the multiple times using the endocardial surface data, wherein the prolate spheroidal coordinates comprise a longitudinal angular coordinate μ, a circumferential angular coordinate θ, and a coordinate λ as a function of longitudinal angular coordinate μ and circumferential angular coordinate θ;

computing a measure based at least in part on the value of coordinate λ at the at least a portion of the multiple times, wherein the measure provides diagnostic information related to the left ventricle; and wherein the multiple times over the heartbeat comprise end diastole and end systole of the heartbeat, wherein generating a representation in prolate spheroidal coordinates of the endocardial surface of the left ventricle comprises generating a representation at end diastole and end systole, such that $\lambda_{ED}$ represents the value of coordinate λ at end diastole and $\lambda_{ES}$ represents the value of coordinate λ at end systole and wherein the measure comprises three-dimensional fractional shortening ("3DFS") of the left ventricle computed as 3DFS=$(\lambda_{ED}-\lambda_{ES})/\lambda_{ED}$.

4. The method of claim 3, further comprising:
providing an indication of the measure on a map of the left ventricle.

5. The method of claim 4, wherein the map comprises an area-preserving map of the left ventricle.

6. The method of claim 4, wherein the map comprises a circumferential polar plot of the left ventricle.

7. The method of claim 3, further comprising:
providing the measure to a mapping application, such that an indication of the measure can be provided on a map of the left ventricle by the mapping application.

8. The method of claim 3, wherein the multiple times over the heartbeat comprise end diastole of the heartbeat.

9. The method of claim 3, wherein the multiple times over the heartbeat comprise end diastole and end systole of the heartbeat.

10. The method of claim 3, wherein the volumetric imaging application is selected from the group consisting of real-time three-dimensional echocardiography, magnetic resonance imaging; x-ray ventriculography, and computed tomography.

11. The method of claim 3, wherein generating a representation in prolate spheroidal coordinates of the endocardial surface of the left ventricle comprises:
converting the endocardial surface data into the prolate spheroidal coordinates; and
fitting the prolate spheroidal coordinates to a finite element mesh representing the endocardial surface of the left ventricle.

12. The method of claim 11, wherein the finite element mesh is constructed from polynomial basis functions.

13. The method of claim 3, wherein the endocardial surface data for the left ventricle of the heart corresponds to spatial coordinates in a spatial coordinate system defining the endocardial surface of the left ventricle, and wherein generating a representation in prolate spheroidal coordinates of the endocardial surface of the left ventricle comprises:
converting the spatial coordinates in the spatial coordinate system to Cartesian coordinates $X_1$, $X_2$, and $X_3$ in a Cartesian coordinate system; and
converting Cartesian coordinates $X_1$, $X_2$, and $X_3$ to the prolate spheroidal coordinates.

14. The method of claim 3, wherein the endocardial surface data for the left ventricle of the heart corresponds to Cartesian coordinates $X_1$, $X_2$, and $X_3$ defining the endocardial surface of the left ventricle, and wherein generating a representation in prolate spheroidal coordinates of the endocardial surface of the left ventricle comprises:
converting Cartesian coordinates $X_1$, $X_2$, and $X_3$ to the prolate spheroidal coordinates, wherein the prolate spheroidal coordinates are defined by transformation equations $X_1 = d \cdot \cos h\lambda \cdot \cos \mu,$ $X_2 = d \cdot \sin h\lambda \cdot \sin \mu \cdot \cos \theta,$ and $X_3 = d \cdot \sin h\lambda \cdot \sin \mu \cdot \sin \theta;$ and wherein the variable d comprises a focal length of the prolate spheroidal representation.

15. The method of claim 3, wherein the multiple times over the heartbeat comprise end diastole of the heartbeat, wherein generating a representation in prolate spheroidal coordinates of the endocardial surface of the left ventricle comprises generating a representation at end diastole and two or more additional times over the heartbeats such that $\lambda_{ED}$ represents the value of coordinate λ at end diastole and $\lambda_{MIN}$ represents the minimum value of coordinate λ over the heartbeat, and wherein the measure comprises four-dimensional fractional shortening ("4DFS") of the left ventricle computed as 4DFS=$(\lambda_{ED}-\lambda_{MIN})/\lambda_{ED}$.

16. The method of claim 15, wherein the minimum value of coordinate λ over the heartbeat $\lambda_{MIN}$ is determined by fitting the prolate spheroidal coordinates to a finite element mesh representing the endocardial surface of the left ventricle.

17. The method of claim 3, wherein the measure comprises a derivative of coordinate λ selected from the group consisting of $\partial\lambda/\partial\mu$, $\partial\lambda/\partial\theta$, $\partial\lambda/\partial t$, $\partial^2\lambda/\partial\mu\partial t$, and $\partial^2\lambda/\partial\theta\partial t$.

18. The method of claim 3, wherein the measure comprises maximum systolic $\partial\lambda/\partial t$ for the heartbeat.

19. The method of claim 3, wherein the diagnostic information related to the left ventricle comprises an indication of size of one or more ischemic regions of the left ventricle.

20. The method of claim 3, wherein the diagnostic information related to the left ventricle comprises an indication of location of one or more ischemic regions of the left ventricle.

21. The method of claim 3, wherein the diagnostic information related to the left ventricle comprises an indication of severity of one or more ischemic regions of the left ventricle.

22. The method of claim 3, wherein the diagnostic information related to the left ventricle comprises an indication of synchrony of contraction of the left ventricle.

23. A non-transitory computer readable medium storing computer executable instructions for providing diagnostic information using endocardial surface data for a patient's heart, the executable instructions comprising:
  generating a representation in prolate spheroidal coordinates of the endocardial surface of the left ventricle of a heart at multiple times over a heartbeat using endocardial surface data, wherein the endocardial surface data is obtained using a volumetric imaging application, and wherein the prolate spheroidal coordinates comprise a longitudinal angular coordinate µ, a circumferential angular coordinate θ, and a coordinate λ as a function of longitudinal angular coordinate µ and circumferential angular coordinate θ;
  computing a measure based at least in part on the value of coordinate λ at the multiple times, wherein the measure provides diagnostic information related to the left ventricle; and
  wherein the multiple times over the heartbeat comprise end diastole and end systole of the heartbeat, wherein generating a representation in prolate spheroidal coordinates of the endocardial surface of the left ventricle comprises generating a representation at end diastole and end systole, such that $\lambda_{ED}$ represents the value of coordinate λ at end diastole and $\lambda_{ES}$ represents the value of coordinate λ at end systole, and wherein the measure comprises three-dimensional fractional shortening ("3DFS") of the left ventricle computed as 3DFS=$(\lambda_{ED}-\lambda_{ES})/\lambda_{ED}$.

24. A method for providing diagnostic information using endocardial surface data for a patient's heart, the method comprising:
  receiving endocardial surface data for the left ventricle of a heart, wherein the endocardial surface data represents the endocardial surface of the left ventricle at multiple times over a heartbeat, and wherein the endocardial surface data is obtained using a volumetric imaging application;
  generating a three-dimensional representation of the endocardial surface of the left ventricle at least a portion of the multiple times using the endocardial surface data, wherein the three-dimensional representation comprises a coordinate λ, that identifies a position of the endocardial surface with respect to a central axis of the left ventricle;
  computing a measure based at least in part on the value of coordinate λ, at the at least a portion of the multiple times, wherein the measure provides diagnostic information related to the left ventricle; and
  wherein the multiple times over the heartbeat comprise end diastole and end systole of the heartbeat, wherein generating a three-dimensional representation of the endocardial surface of the left ventricle comprises generating a three-dimensional representation at end diastole and end systole, such that $\lambda_{ED}$ represents the value of coordinate λ at end diastole and $\lambda_{ES}$ represents the value of coordinate λ at end systole, and wherein the measure comprises three-dimensional fractional shortening ("3DFS") of the left ventricle computed as 3DFS= $(\lambda_{ED}-\lambda_{ES})/\lambda_{ED}$.

25. The method of claim 24, wherein generating a three-dimensional representation of the endocardial surface comprises generating a three-dimensional representation in prolate spheroidal coordinates, the prolate spheroidal coordinates comprising a longitudinal angular coordinate µ, a circumferential angular coordinate θ, and the coordinate λ as a function of longitudinal angular coordinate µ and circumferential angular coordinate θ.

26. The method of claim 24, wherein the multiple times over the heartbeat comprise end diastole of the heartbeat, wherein generating a three-dimensional representation of the endocardial surface of the left ventricle comprises generating a three-dimensional representation at end diastole and two or more additional times over the heartbeat, such that $\lambda_{ED}$ represents the value of coordinate λ at end diastole and $\lambda_{MIN}$ represents the minimum value of coordinate λ over the heartbeat, and wherein the measure comprises four-dimensional fractional shortening ("4DFS") of the left ventricle computed as 4DFS=$(\lambda_{ED}-\lambda_{MIN})/\lambda_{ED}$.

* * * * *